US012740941B2

(12) United States Patent
Graham et al.

(10) Patent No.: US 12,740,941 B2
(45) Date of Patent: Sep. 22, 2026

(54) OPHTHALMIC PHARMACEUTICAL COMPOSITIONS OF ROFLUMILAST

(71) Applicant: Iolyx Therapeutics, Inc., Burlingame, CA (US)

(72) Inventors: Richard Graham, Irvine, CA (US); Hovhannes J. Gukasyan, Orange, CA (US); Elizabeth W. Jeffords, Hillsborough, CA (US); Bhaskar Chaudhuri, San Jose, CA (US)

(73) Assignee: IOLYX THERAPEUTICS, INC., Burlingame, CA (US)

( * ) Notice: Subject to any disclaimer, the term of this patent is extended or adjusted under 35 U.S.C. 154(b) by 0 days.

(21) Appl. No.: 17/948,550

(22) Filed: Sep. 20, 2022

(65) Prior Publication Data

US 2023/0088371 A1 Mar. 23, 2023

Related U.S. Application Data

(60) Provisional application No. 63/261,404, filed on Sep. 20, 2021.

(51) Int. Cl.

| | |
|---|---|
| ***A61K 9/08*** | (2006.01) |
| ***A61K 9/00*** | (2006.01) |
| ***A61K 31/44*** | (2006.01) |
| ***A61K 47/12*** | (2006.01) |
| ***A61K 47/26*** | (2006.01) |
| ***A61K 47/32*** | (2006.01) |
| ***A61K 47/34*** | (2017.01) |
| ***A61K 47/38*** | (2006.01) |

(52) U.S. Cl.

CPC .............. *A61K 9/08* (2013.01); *A61K 9/0048* (2013.01); *A61K 31/44* (2013.01); *A61K 47/12* (2013.01); *A61K 47/26* (2013.01); *A61K 47/32* (2013.01); *A61K 47/34* (2013.01); *A61K 47/38* (2013.01)

(58) Field of Classification Search

CPC ........ A61K 9/08; A61K 9/0048; A61K 31/44; A61K 47/12; A61K 47/26; A61K 47/32; A61K 47/34; A61K 47/38

See application file for complete search history.

(56) References Cited

U.S. PATENT DOCUMENTS

| | | | |
|---|---|---|---|
| 5,712,298 | A | 1/1998 | Amschler |
| 6,872,382 | B1 | 3/2005 | Gamache et al. |
| 7,576,069 | B2 | 8/2009 | Rieger et al. |
| 7,605,143 | B2 | 10/2009 | Rieger et al. |
| 8,497,379 | B2 | 7/2013 | Choi-Sledeski et al. |
| 8,614,210 | B2 | 12/2013 | Bhutada et al. |
| 8,663,694 | B2 | 3/2014 | Brück-Scheffler et al. |
| 9,115,133 | B2 | 8/2015 | Barawkar et al. |
| 9,192,623 | B2 | 11/2015 | Scott |
| 12,102,622 | B2 | 10/2024 | Chaudhuri et al. |
| 12,263,160 | B2 | 4/2025 | Jeffords et al. |
| 2002/0035264 | A1 | 3/2002 | Kararli et al. |
| 2006/0084684 | A1 | 4/2006 | Bolle et al. |
| 2006/0084685 | A1 | 4/2006 | Koenen et al. |
| 2006/0257486 | A1 | 11/2006 | Owen et al. |
| 2007/0203209 | A1 | 8/2007 | Bartolini et al. |
| 2007/0259009 | A1 | 11/2007 | Linder |
| 2008/0255209 | A1 | 10/2008 | Klein et al. |
| 2009/0186923 | A1 | 7/2009 | Armer et al. |
| 2009/0209599 | A1 | 8/2009 | Endo et al. |
| 2011/0086023 | A1 | 4/2011 | Lane |
| 2012/0283252 | A1* | 11/2012 | Bhutada .................. A61P 27/02 514/226.5 |
| 2014/0155381 | A1 | 6/2014 | Baloglu et al. |
| 2015/0125539 | A1* | 5/2015 | Popov .................. A61K 9/5146 424/497 |
| 2015/0272936 | A1 | 10/2015 | Vakkalanka et al. |
| 2015/0366890 | A1 | 12/2015 | Collins et al. |
| 2016/0045508 | A1 | 2/2016 | Vazquez et al. |
| 2019/0192691 | A1 | 6/2019 | Barrett et al. |

(Continued)

FOREIGN PATENT DOCUMENTS

| | | | |
|---|---|---|---|
| EP | 1796668 | B1 | 9/2008 |
| EP | 1906916 | B1 | 10/2008 |

(Continued)

OTHER PUBLICATIONS

Mohr et al., Gamma irradiation for terminal sterilization of 17b-estradiol loaded poly-(D, L-lactide-co-glycolide) microparticles, Journal of Controlled Release 61 (1999) 203-217 (Year: 1999).*
Wiley A. Chambers, MD. Clinical Review #2 for NDA 208144. Feb. 27, 2017. (Year: 2017).*
Kalepu et al., Review. Insoluble drug delivery strategies: review of recent advances and business prospects. Acta Pharmaceutica Sinica B 2015;5(5):442-453 (Year: 2015).*
Mohr et al., Gamma irradiation for terminal sterilization of 17b-estradiol oaded poly-(D, L-lactide-co-glycolide) microparticles. Journal of Controlled Release 61 (1999) 203â217 (Year: 1999).*
Sakkas et al., "Phosphodiesterase 4 Inhibitors in Immune-mediated Diseases: Mode of Action, Clinical Applications, Current and Future Perspectives," Current Medicinal Chemistry (2017), 24, 3054-3067.

(Continued)

*Primary Examiner* — Robert A Wax
*Assistant Examiner* — Ngoc-Anh Thi Nguyen
(74) *Attorney, Agent, or Firm* — Rothwell, Figg, Ernst & Manbeck, P.C.

(57) ABSTRACT

The present invention relates to stable, ophthalmic pharmaceutical formulations of the phosphodiesterase-4 inhibitor, roflumilast, and methods of making the same. Novel ophthalmic pharmaceutical formulations of roflumilast can comprise a viscosity agent, a surfactant, and a buffer. In preferred embodiments, the pH of the ophthalmic pharmaceutical composition is between 6.0 and 6.7. Methods of making stable, ophthalmic pharmaceutical formulations of roflumilast can include separate active and inactive ingredient processes. Further, the methods can include clarity filtration to mitigate particle size aggregation and to create an optimized suspension. Further, the methods can include terminal sterilization of the final drug product.

22 Claims, 26 Drawing Sheets

(56) References Cited

U.S. PATENT DOCUMENTS

| | | | |
|---|---|---|---|
| 2020/0129461 A1 | 4/2020 | Bannister et al. | |
| 2021/0244718 A1 | 8/2021 | Osborne | |
| 2021/0346661 A1* | 11/2021 | Johnson | A61K 31/683 |

FOREIGN PATENT DOCUMENTS

| | | | | |
|---|---|---|---|---|
| EP | 1511516 B1 | 12/2008 | | |
| EP | 2020243 A1 | 2/2009 | | |
| EP | 1511481 B1 | 10/2010 | | |
| EP | 2020243 B1 | 8/2018 | | |
| JP | 2005-529928 A | 10/2005 | | |
| JP | 2007-16024 A | 1/2007 | | |
| WO | 9841232 A2 | 9/1998 | | |
| WO | WO-03099278 A1 * | 12/2003 | | A61K 31/44 |
| WO | 2006032675 A1 | 3/2006 | | |
| WO | 2006121963 A2 | 11/2006 | | |
| WO | 2015132708 A1 | 9/2015 | | |
| WO | 2016/152821 A1 | 9/2016 | | |
| WO | 2017072131 A1 | 5/2017 | | |
| WO | 2020/223279 A1 | 11/2020 | | |
| WO | 2021100051 A1 | 5/2021 | | |

OTHER PUBLICATIONS

Tan et al., "Analysis of Th17-associated cytokines in tears of patients with dry eye syndrome," Eye (2014), 28, 608-613.

Liu et al., "Analysis of Th17-associated cytokines and clinical correlations in patients with dry eye disease," Plos One 12(4) (Apr. 5, 2017), 12 pages.

Riemens et al., "Cytokines in tear fluid of patients with ocular graft-versus-host disease after allogeneic stem cell transplantation, " Molecular Vision (2012), 18:797-802.

Rajasagi et al., "The Role of T Cells in Herpes Stromal Keratitis," Frontiers in Immunology, (Mar. 2019), vol. 10, Article 512, 7 pages.

Walscheid et al., "Increased Circulating Proinflammatory T Lymphocytes in Children with Different Forms of Anterior Uveitis: Results from a Pilot Study," Ocul Immunol Inflamm. (2019), 27(5):788-797, 2 pages.

Fung et al., "Local delivery of corticosteroids in clinical ophthalmology: A review," Clin. Experiment Ophthalmol. (2020), 48:366-401.

Kaiko et al., "Immunological decision-making: how does the immune system decide to mount a helper T-cell response?," Immunology, (2007); 123(3): 326-338.

Kim et al., "Tear cytokines and chemokines in patients with Demodex blepharitis," Cytokine, 53, (2011), 94-99.

Allergan, Prescribing Information for Pred Forte (prednisolone acetate ophthalmic suspension, USP) 1% sterile (2017), 5 pages.

Agarwal et al., "Formulation Considerations for the Management of Dry Eye Disease," Pharmaceutics, 13, 207 (Feb. 3, 2021), 19 pages.

International Search Report and the Written Opinion of the International Searching Authority, issued in corresponding International Application No. PCT/US2022/076726, dated Nov. 25, 2022, 20 pages.

International Search Report and the Written Opinion of the International Searching Authority, issued in corresponding International Application No. PCT/US2022/076826, dated Dec. 15, 2022, 17 pages.

Final Office Action mailed Nov. 29, 2023 in corresponding U.S. Appl. No. 17/950,802, First Named Inventor: Elizabeth W. Jeffords (10 pages).

Non-Final Office Action mailed Feb. 16, 2024 in corresponding U.S. Appl. No. 17/668,858, First Named Inventor: Bhaskar Chaudhuri (9 pages).

Loch, et al., "Determination of permeability coefficients of ophthalmic drugs through different layers of porcine, rabbit and bovine eyes", European Journal of Pharmaceutical Sciences 47 (2012) 131-138. (8 pages).

Toropainen, et al., "Biopharmaceutics of Topical Ophthalmic Suspensions: Importance of Viscosity and Particle Size in Ocular Absorption of Indomethacin", Pharmaceutics 2021, 13, 452. (13 pages).

Non-Final Office Action mailed May 22, 2024 in corresponding U.S. Appl. No. 17/950,802, First Named Inventor: Elizabeth W. Jeffords (15 pages).

Vázquez-Blanco et al., "pH determination as a quality standard for the elaboration of oral liquid compounding formula", Farmacia HOSPITALARIA, 2018;42(6):221-227 (7 pages).

The extended European search report mailed Feb. 11, 2025 in corresponding European Patent Application No. 22871027.3 (10 pages).

International Search Report and the Written Opinion of the International Searching Authority, issued in corresponding International Application No. PCT/US2022/076876, dated Dec. 15, 2022, 17 pages.

Saricay et al., "Concurrent ocular pain in patients with neurotrophic keratopathy", The Ocular Surface 22 (2021) 143-151 (9 pages).

First Examination Report (FER) mailed Jan. 13, 2026 in corresponding Indian Patent Application No. 202427029493 (7 pages).

* cited by examiner

Particle Size Distribution Plot for Roflumilast CMC Composition Under Autoclaved Conditions Particle Size Distribution Plot for Roflumilast CMC Compositions
Under Autoclaved and Non-Autoclaved Conditions After Stirring pre-autoclave stirred 60 min pre-autoclave stirred overnight autoclave stirred overnight Particle Size Distribution Plots of Roflumilast Compositions Following Terminal Gamma Radiation d(0.1): 2.437 um d(0.5): 4.353 um d(0.9): 8.058 um d(0.1): 2.240 um d(0.5): 3.816 um d(0.9): 6.711 um Particle Size Distribution Plots of Roflumilast Compositions Following Terminal Gamma Radiation d(0.1): 2.126 um d(0.5): 3.834 um d(0.9): 7.216 um d(0.1): 2.246 um d(0.5): 3.914 um d(0.9): 7.161 um

OPHTHALMIC PHARMACEUTICAL COMPOSITIONS OF ROFLUMILAST

CROSS REFERENCE TO RELATED APPLICATIONS

The present application claims priority to U.S. Provisional Application No. 63/261,404 filed on Sep. 20, 2021, which is incorporated by reference herein.

FIELD OF THE INVENTION

The present invention relates to stable and pharmaceutically effective ophthalmic compositions of the phosphodiesterase-4 inhibitor, roflumilast. More specifically, the invention relates to novel ophthalmic pharmaceutical compositions of roflumilast comprising a viscosity agent, a surfactant, and a buffer. Additionally, the present invention includes methods of manufacturing pharmaceutically effective ophthalmic compositions of roflumilast, which optimize the potency and purity of the composition.

BACKGROUND OF THE INVENTION

Roflumilast is a potent and selective long-acting inhibitor of phosphodiesterase (PDE) type 4, with anti-inflammatory and potential antineoplastic activities. Roflumilast is known to be suitable as a bronchial therapeutic agent as well as for the treatment of inflammatory disorders. Compositions containing roflumilast are used in human and veterinary medicine and have been proposed for the treatment and prophylaxis of diseases including but not limited to: inflammatory and allergen-induced airway disorders (e.g., bronchitis, asthma, COPD), dermatoses (e.g., proliferative, inflammatory, and allergen induced skin disorders), and generalized inflammations in the gastrointestinal region (Crohn's disease and ulcerative colitis). Oral pharmaceutical compositions of roflumilast are currently marketed under the tradenames Daliresp® (in the United States) and Daxas® (in Europe) for COPD, and topical compositions of roflumilast cream for dermatological use are currently marketed under the tradename Zoryve™ (in the United States) for psoriasis.

Roflumilast and its synthesis are described in U.S. Pat. No. 5,712,298. It has been recognized that pharmaceutical compounds having phosphodiesterase (PDE)-4 inhibiting properties, such as roflumilast, are therapeutically effective and useful for treating inflammatory disorders, such as psoriasis and atopic dermatitis. While the therapeutic effectiveness of oral and dermal pharmaceutical compositions have been studied, there is a need for ophthalmic pharmaceutical compositions of roflumilast suitable for treating inflammatory or immune-mediated disorders of the eye. The majority of the market for anti-inflammatory ocular drugs today is based around antibiotics/anti-microbials (in the context of infectious/inflammatory indications), immunomodulatory agents (including immunosuppressants and corticosteroids), and non-steroidal anti-inflammatory agents. These main classes of agents typically do not meet the clinical needs of mid to long-term inflammatory disease, or present significant comorbidity and safety issues. As such, there is a high unmet need for an anti-inflammatory roflumilast ophthalmic formulation in a convenient and tolerable form.

The delivery of drugs to the eye is very difficult, as pharmaceutical ophthalmic agents must balance tolerability, sterility, safety, and efficacy. Priyanka Agarwal et al., *Formulation Considerations for the Management of Dry Eye*

*Disease*, Pharmaceutics, 13, 207 (Feb. 3, 2021) discusses the formulation challenges for ophthalmic pharmaceutical formulations. For example, there can be poor tolerability of formulation excipients. Additionally, poor patient compliance is frequently a challenge with ophthalmic pharmaceutical formulations. Developing a stable ophthalmic formulation which can be manufactured under sterile conditions while retaining physicochemical properties of the active agent, staying within a tight range of pH and inactive ingredients which are tolerable to the eye, and which can be delivered in effective doses to the eye is very difficult. Ophthalmic delivery is focused on either the ocular surface, the anterior, or posterior segment of the eye. Ocular surface formulations, often delivered by the patient one to four or more times a day, have the additional challenge of requiring dosing consistency and yet flexibility to deliver effective dose despite common operator errors found in home-based patient delivery: sterility issues, variance in delivery volume, and accuracy in placement. Patients with long-term ocular disease also have increased sensitivity to active and inactive ingredients and preservatives, creating additional formulation challenges.

SUMMARY OF THE INVENTION

The present invention relates to stable ophthalmic pharmaceutical compositions of the phosphodiesterase-4 inhibitor, roflumilast. In certain embodiments, the ophthalmic pharmaceutical formulation of roflumilast comprises a viscosity agent, a surfactant, and a buffer. The inventors of the subject application have found that due to extremely low solubility of roflumilast at the target pH of tolerable ocular delivery, it is indeed quite difficult to create conditions in which roflumilast will stay in suspension with optimal potency, particle size distribution, low level of degradants, optimal resuspendability, and ability to maintain stability through aseptic conditions. The inventors have found there are very limited conditions and processes in which a clinically suitable formulation can be created. The formulations of the present invention can address these problems and issues within a range of roflumilast concentrations.

The inventors of the subject application have identified that roflumilast undergoes hydrolysis at low potencies in certain ophthalmic pharmaceutical compositions. The inventors of the subject application have discovered the ophthalmic pharmaceutical compositions of the present invention can reduce the rate of hydrolysis. In certain embodiments, the pH of the ophthalmic pharmaceutical compositions is between about 6.0 and 6.7, which can reduce the rate of hydrolysis of roflumilast, thereby minimizing the rate of other substances in the agent, and enhancing product purity and potency.

An embodiment of the present invention provides for an ophthalmic pharmaceutical composition comprising a therapeutically effective amount of roflumilast, a viscosity agent comprising hydroxypropyl methylcellulose, a surfactant, and a buffer. In certain embodiments, the surfactant is a polysorbate. In certain embodiments, the buffer is a phosphate and citrate buffer. In certain embodiments, the pharmaceutical composition is a suspension. In preferred embodiments, the pharmaceutical composition has a particle size distribution characterized by a d90 value of from about 5 μm to about 25 μm, or more preferably, less than or equal to about 10 μm.

Another embodiment of the present invention provides for an ophthalmic pharmaceutical composition comprising a therapeutically effective amount of roflumilast, a viscosity agent comprising hydroxyethyl cellulose, a surfactant, and a buffer. In certain embodiments, the surfactant is a polysorbate. In certain embodiments, the buffer is a phosphate and citrate buffer. In certain embodiments, the pharmaceutical composition is a suspension. In preferred embodiments, the pharmaceutical composition has a particle size distribution characterized by a d90 value of from about 5 μm to about 25 μm, or more preferably, less than or equal to about 10 μm.

Another embodiment of the present invention provides for an ophthalmic pharmaceutical composition comprising a therapeutically effective amount of roflumilast, a viscosity agent comprising polyvinylpyrrolidone, a surfactant, and a buffer. In certain embodiments, the surfactant is a tyloxapol. In certain embodiments, the buffer is a phosphate and citrate buffer. In certain embodiments, the pharmaceutical composition is a suspension. In preferred embodiments, the pharmaceutical composition has a particle size distribution characterized by a d90 value of from about 5 μm to about 25 μm, or more preferably, less than or equal to about 10 μm.

Yet another embodiment of the present invention provides for an ophthalmic pharmaceutical composition comprising a therapeutically effective amount of roflumilast, a viscosity agent comprising carboxymethyl cellulose, a surfactant, and a buffer. In certain embodiments, the surfactant is a polysorbate. In certain embodiments, the buffer is a phosphate and citrate buffer. In certain embodiments, the pharmaceutical composition is a suspension. In preferred embodiments, the pharmaceutical composition has a particle size distribution characterized by a d90 value of from about 5 μm to about 25 μm, or more preferably, less than or equal to about 10 μm.

Another embodiment of the present invention provides a stable, sterile ophthalmic ointment composition comprising a therapeutically effective amount of roflumilast, petrolatum, and mineral oil. In certain embodiments, the composition comprises from about 0.1% to about 1.0% w/w of roflumilast, about 75% to about 85% w/w of petrolatum, and about 20 to about 25% w/w mineral oil.

Another embodiment of the present invention provides methods of manufacturing a stable, ophthalmic pharmaceutical composition of roflumilast under aseptic conditions. The method includes: (a) sterilizing roflumilast using a form of heat or radiation sterilization; (b) autoclave sterilizing at least one inactive ingredient selected form the group consisting of a viscosity agent, a surfactant, and a buffer; and (c) mixing the sterilized roflumilast and at least one sterilized inactive ingredient to create the stable, ophthalmic pharmaceutical composition of roflumilast. In certain embodiments, the roflumilast is sterilized using dry heat sterilization at a temperature less than the melting point of roflumilast. In certain embodiments, a low-level gamma radiation is used to sterilize the roflumilast. In certain embodiments, the ophthalmic pharmaceutical composition of roflumilast is a suspension.

Another embodiment of the present invention provides a method of manufacturing a stable, ophthalmic pharmaceutical composition of roflumilast comprising: (a) mixing roflumilast and at least one sterilized inactive ingredient to obtain a pharmaceutical composition; (b) packaging the pharmaceutical composition; and (c) terminally sterilizing the pharmaceutical composition in the packaging by using gamma radiation.

Another embodiment of the present invention provides methods of manufacturing a stable, ophthalmic pharmaceutical suspension of roflumilast, whereby for further reducing particle size of the ophthalmic pharmaceutical composition of roflumilast. In certain embodiments, the method further includes a step of filtering the stable, ophthalmic pharmaceutical composition of roflumilast using clarity filtration to produce a suspension having a particle size distribution characterized by a d90 value of less than or equal to about 10 μm.

BRIEF DESCRIPTION OF THE DRAWINGS

The accompanying drawings, which are incorporated herein and form part of the disclosure, help illustrate various embodiments of the present invention and, together with the description, further serve to describe the invention to enable a person skilled in the pertinent art to make and use the embodiments disclosed herein. The error bars in the drawings are standard deviation values.

Figure 6A:
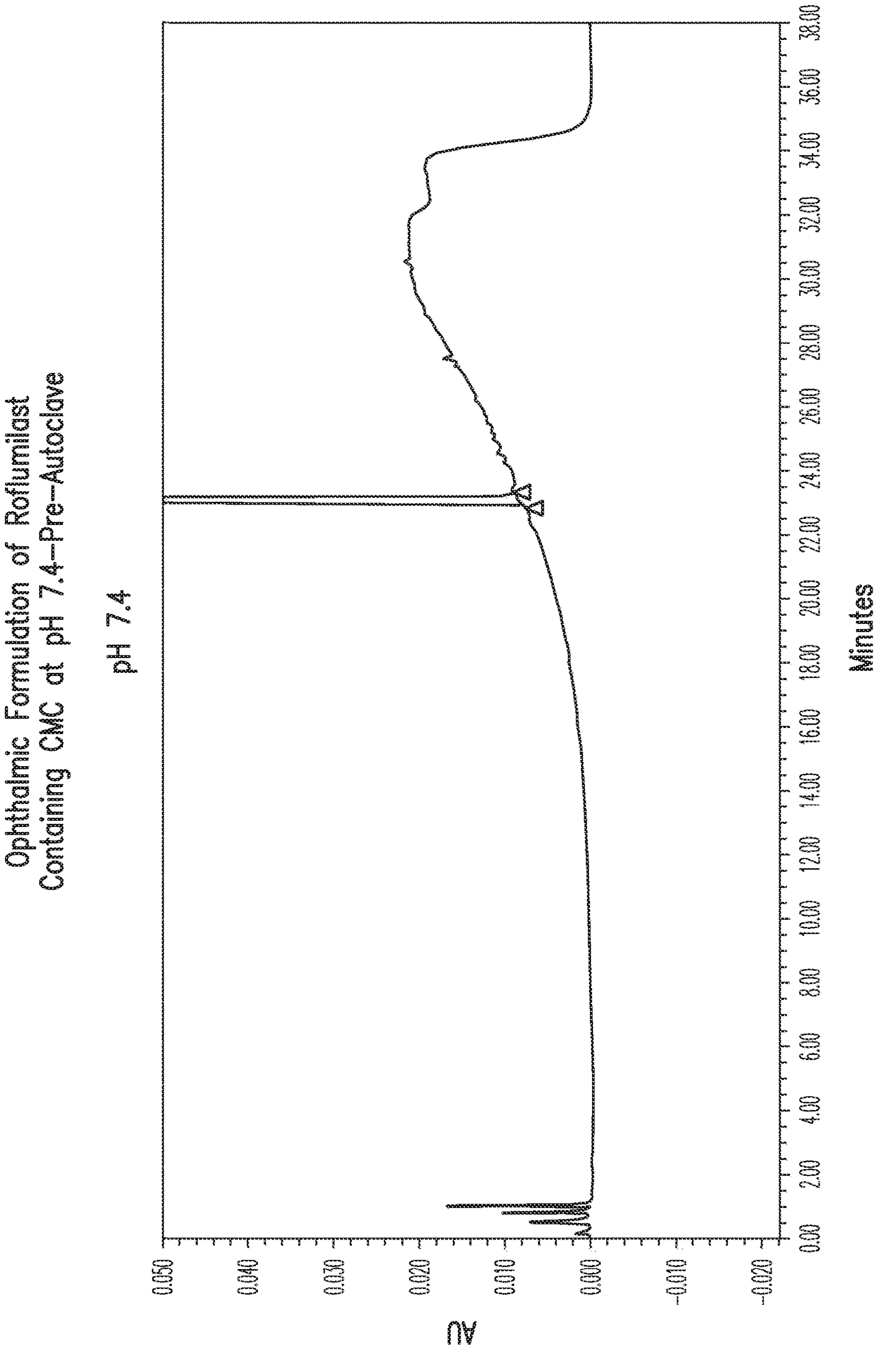
FIG. 6A is an HPLC chromatogram for an exemplary ophthalmic pharmaceutical composition comprising 0.10% roflumilast, 0.50% carboxymethyl cellulose, 0.1% polysorbate, 0.45% phosphate, and 0.05% citrate at a pH of 7.4 under pre-autoclave conditions.
Figure 6B:
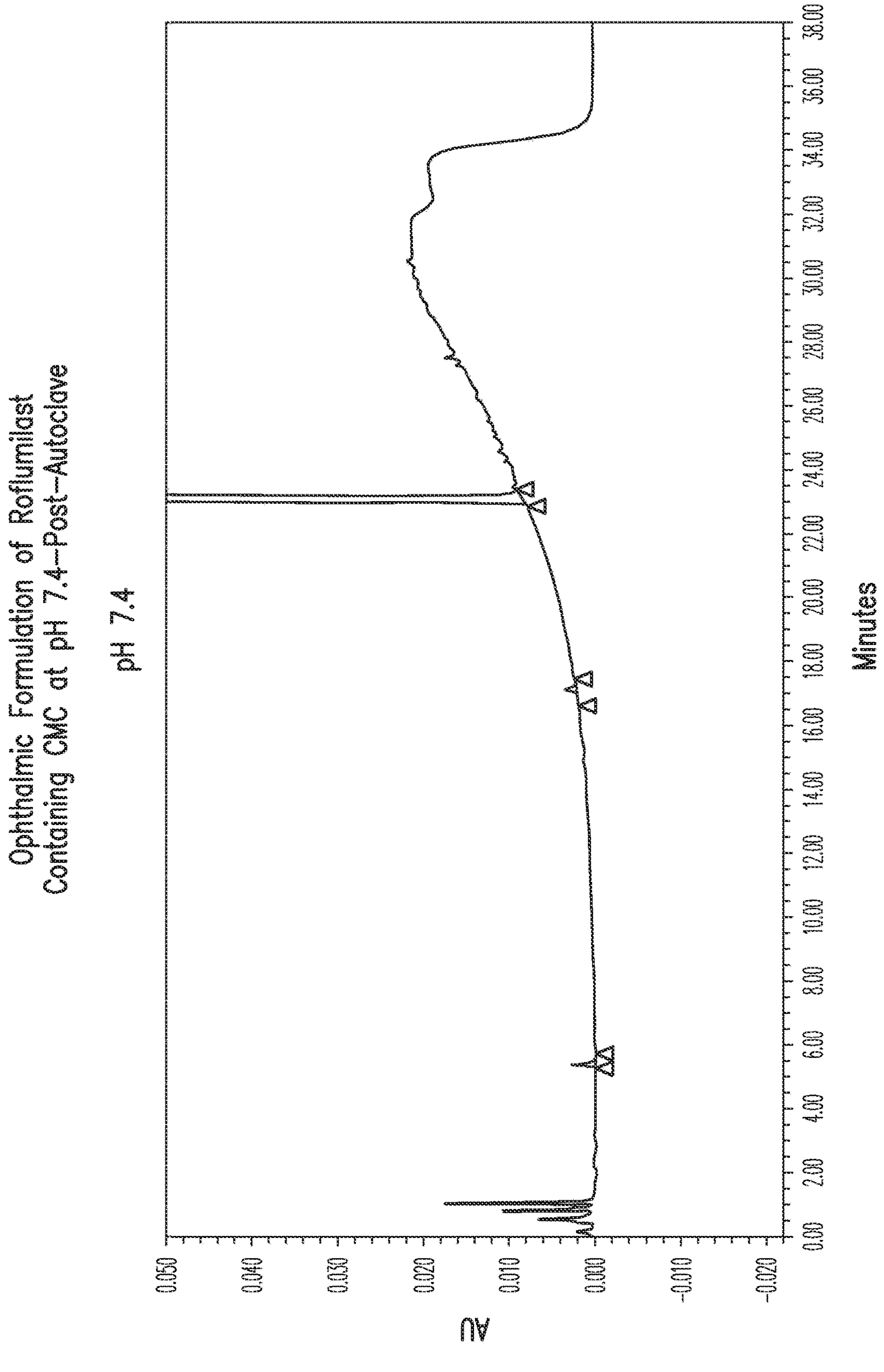
FIG. 6B is an HPLC chromatogram for an exemplary ophthalmic pharmaceutical composition comprising 0.10% roflumilast, 0.50% carboxymethyl cellulose, 0.1% polysorbate, 0.45% phosphate, and 0.05% citrate at a pH of 7.4 under post-autoclave conditions.
Figure 6C:
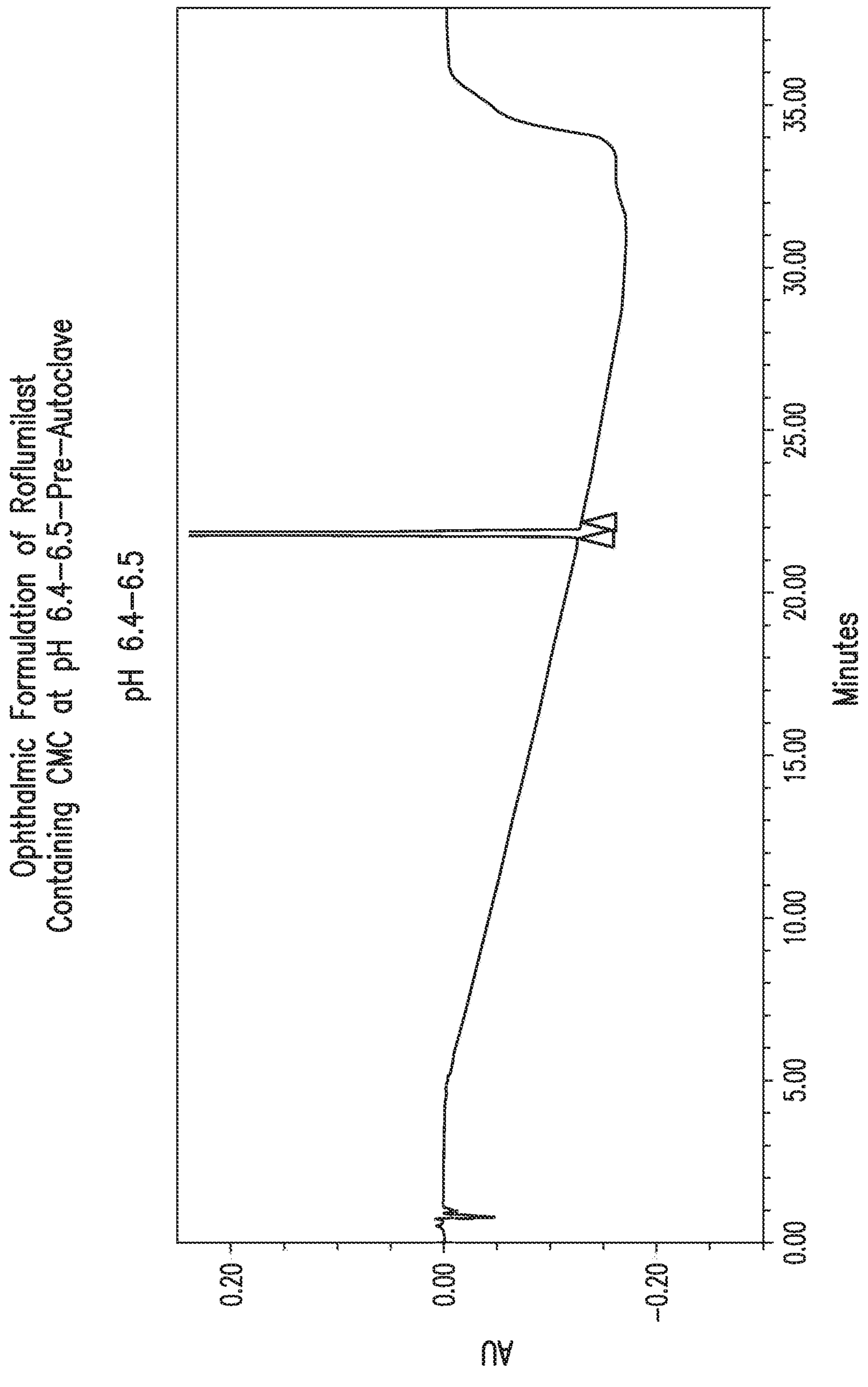
FIG. 6C is an HPLC chromatogram for an exemplary ophthalmic pharmaceutical composition comprising 0.10% roflumilast, 0.50% carboxymethyl cellulose, 0.1% polysorbate, 0.45% phosphate, and 0.05% citrate at a pH of 6.4-6.5 under pre-autoclave conditions.
Figure 6D:
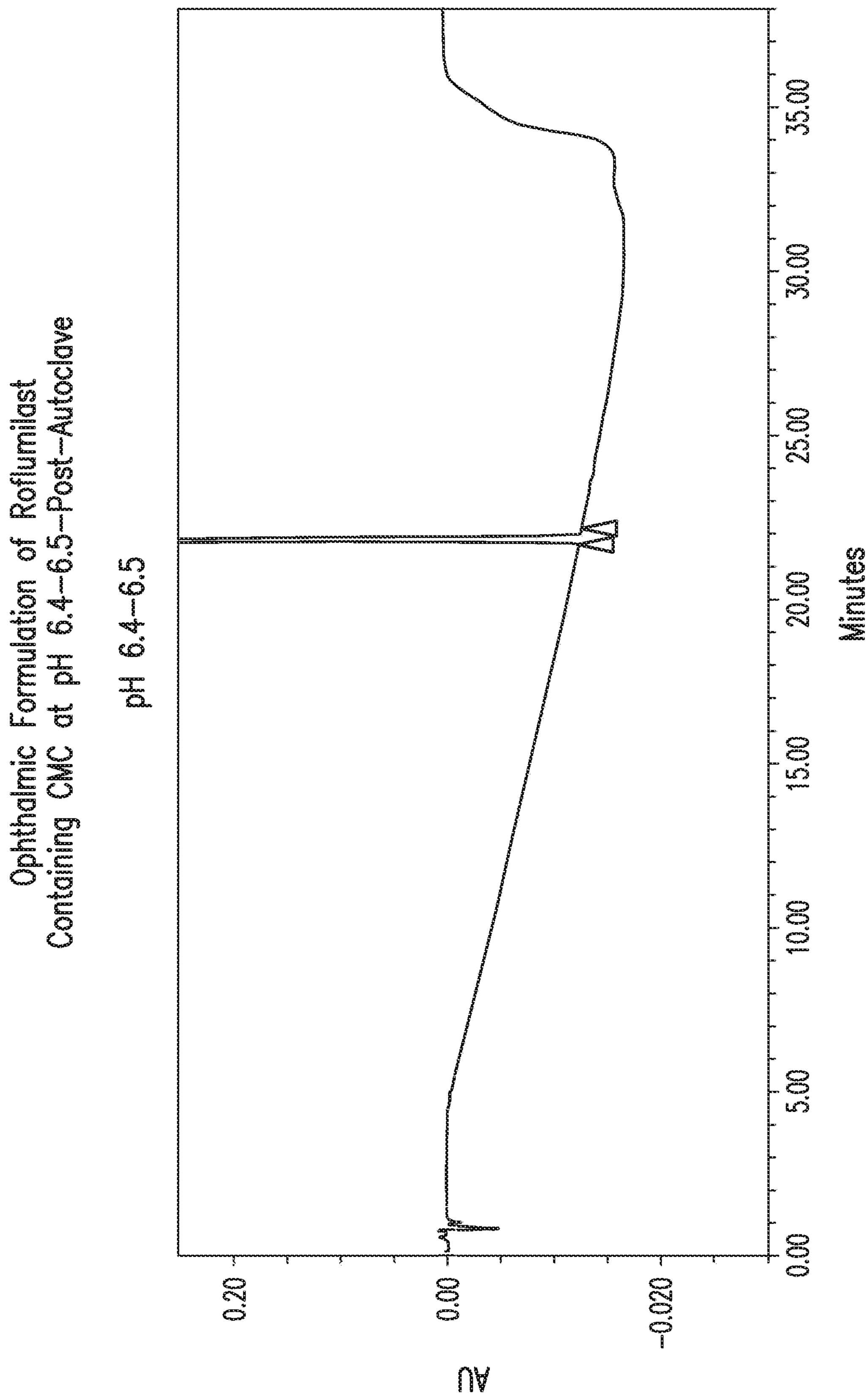

FIG. 6D is an HPLC chromatogram for an exemplary ophthalmic pharmaceutical composition comprising 0.10% roflumilast, 0.50% carboxymethyl cellulose, 0.1% polysorbate, 0.45% phosphate, and 0.05% citrate at a pH of 6.4-6.5 under post-autoclave conditions.

Figure 7:
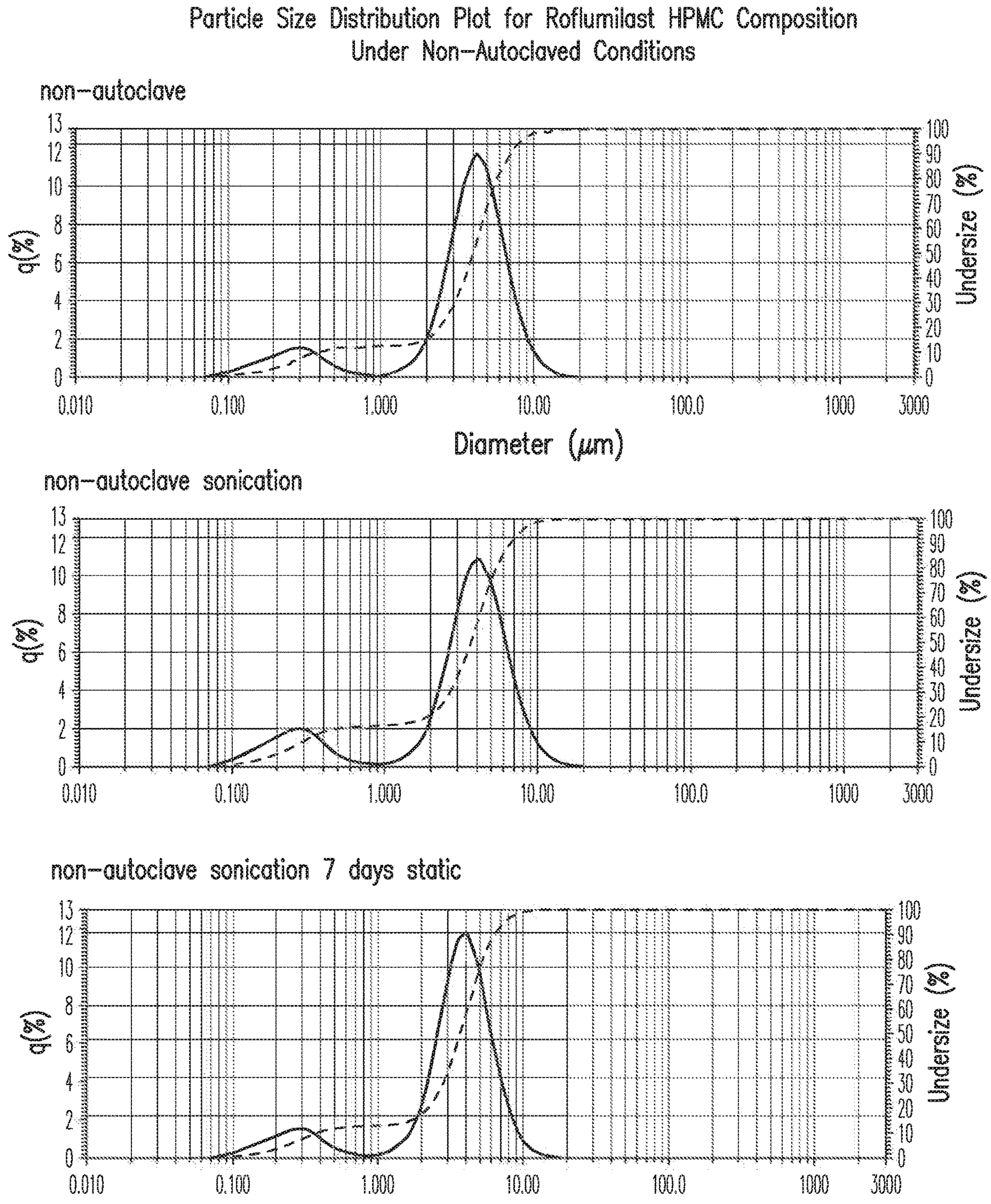

FIG. 7 is particle size distribution plots for an ophthalmic pharmaceutical composition comprising 0.10% roflumilast, 0.30% hydroxypropyl methylcellulose, 0.1% polysorbate, 0.45% phosphate, and 0.05% citrate at a pH of 7.4 comparing non-autoclaved conditions with mixing and 7 days of storage.

Figure 8:
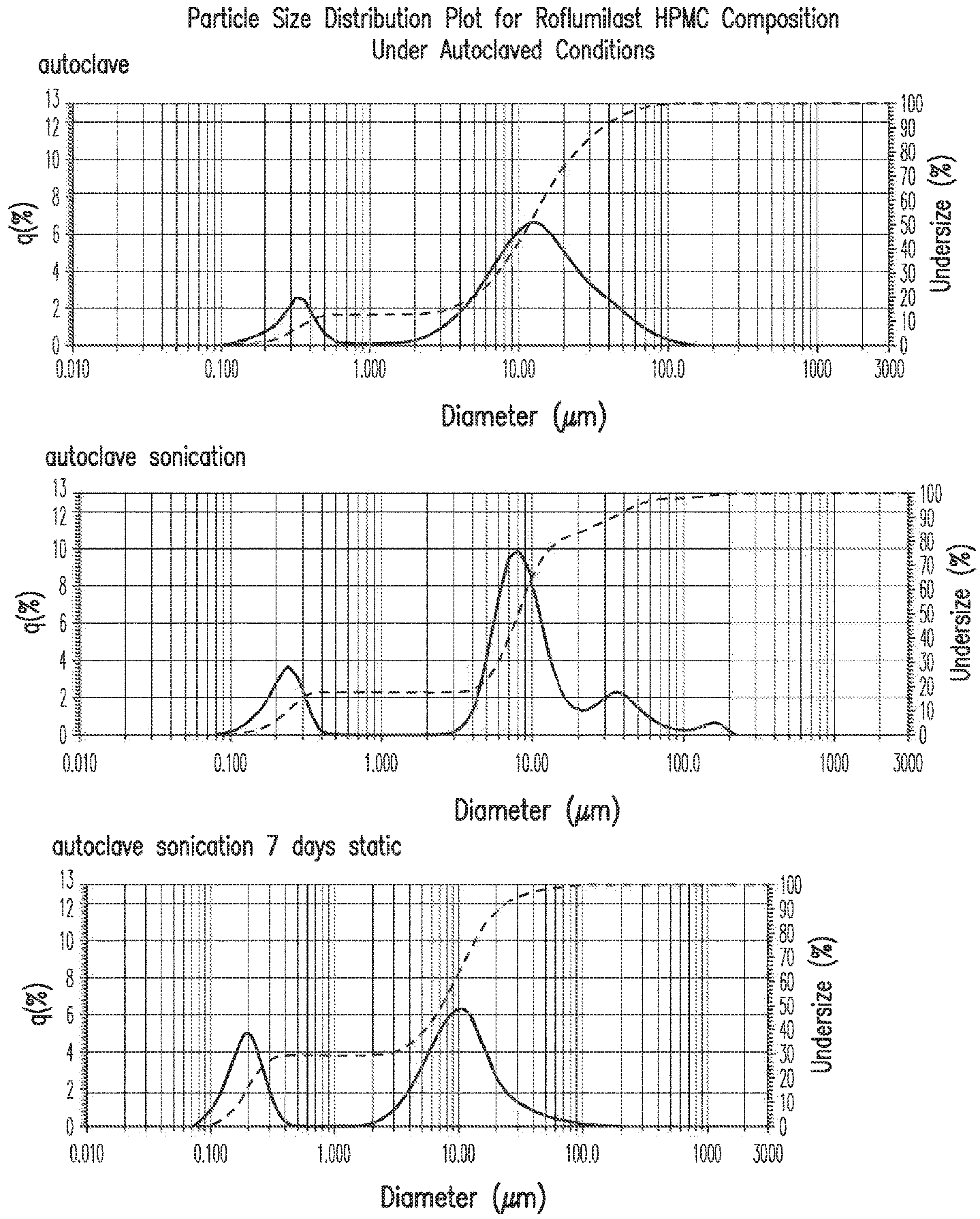

FIG. 8 is particle size distribution plots for an ophthalmic pharmaceutical composition comprising 0.10% roflumilast, 0.30% hydroxypropyl methylcellulose, 0.1% polysorbate, 0.45% phosphate, and 0.05% citrate at a pH of 7.4 comparing autoclaved conditions with mixing and 7 days of storage.

Figure 9:
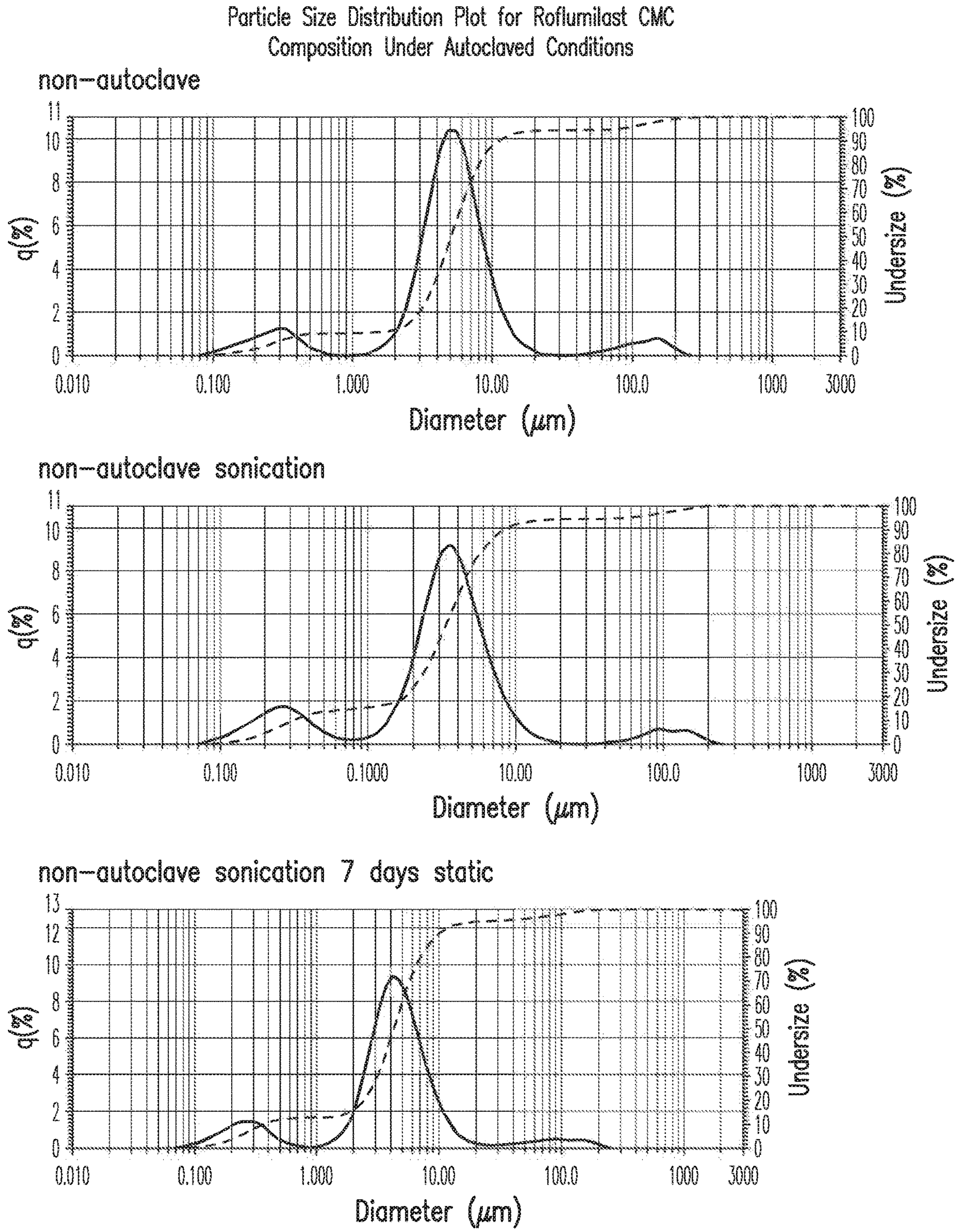

FIG. 9 is particle size distribution plots for an ophthalmic pharmaceutical composition comprising 0.10% roflumilast, 0.50% carboxymethyl cellulose, 0.1% polysorbate, 0.45% phosphate, and 0.05% citrate at a pH of 7.4 comparing non-autoclaved conditions with mixing and 7 days of storage.

Figure 10:
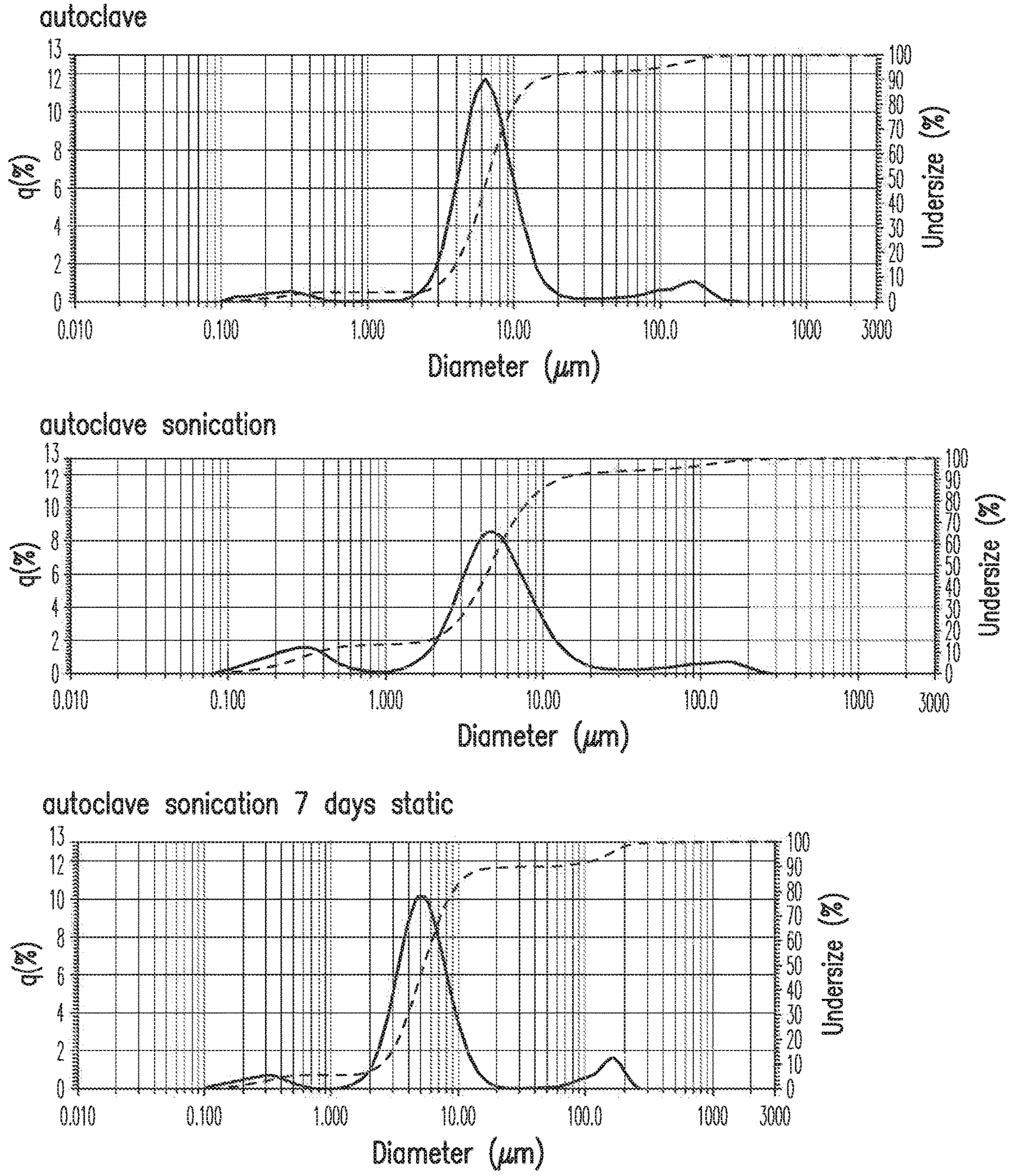

FIG. 10 is particle size distribution plots for an ophthalmic pharmaceutical composition comprising 0.10% roflumilast, 0.50% carboxymethyl cellulose, 0.1% polysorbate, 0.45% phosphate, and 0.05% citrate at a pH of 7.4 comparing autoclaved conditions with mixing and 7 days of storage.

Figure 11:
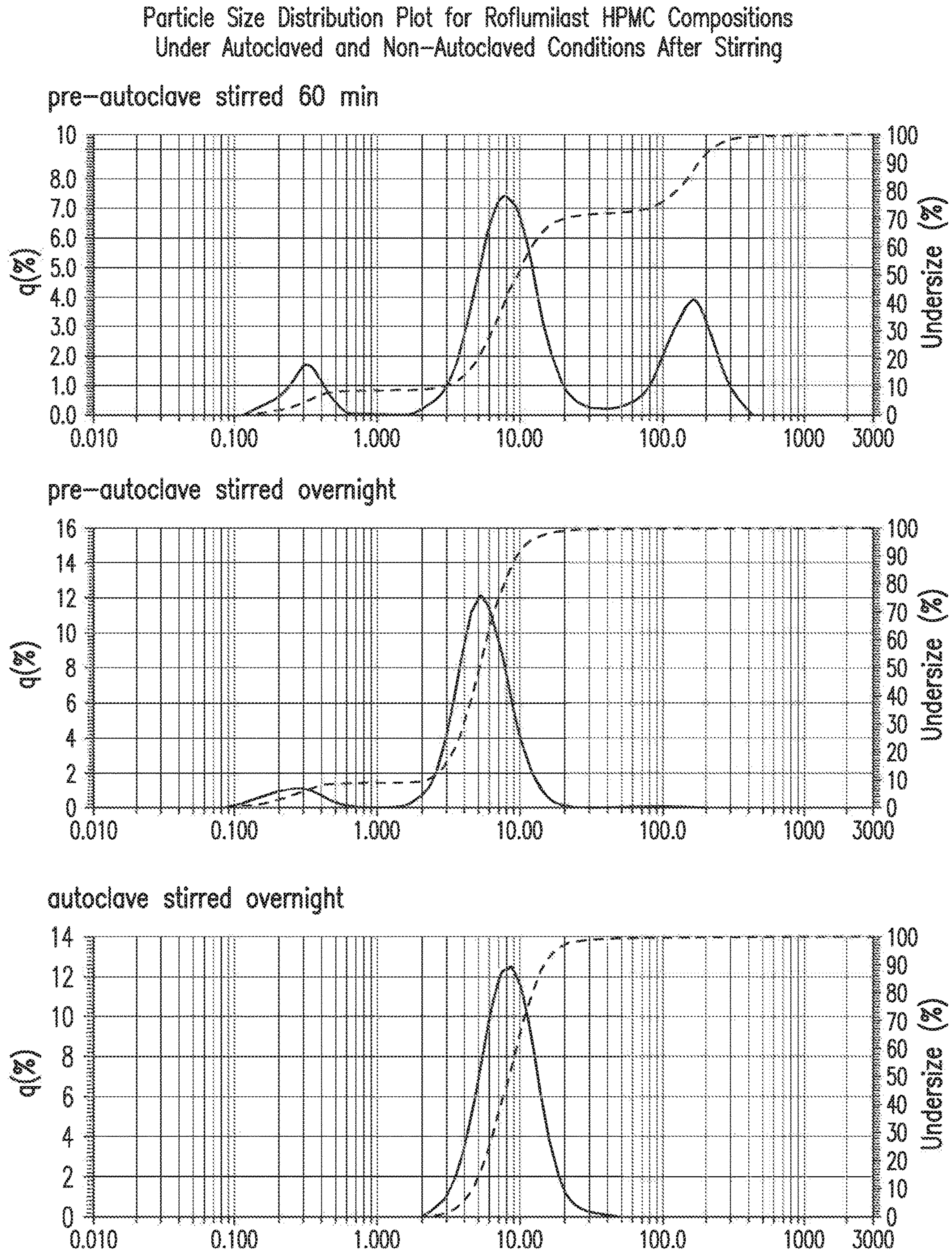

FIG. 11 is particle size distribution plots for an ophthalmic pharmaceutical composition comprising 0.10% roflumilast, 0.30% hydroxypropyl methylcellulose, 0.1% polysorbate, 0.45% phosphate, and 0.05% citrate at a pH of 6.4-6.5, which compares non-autoclaved and autoclaved conditions with stirring.

Figure 12:
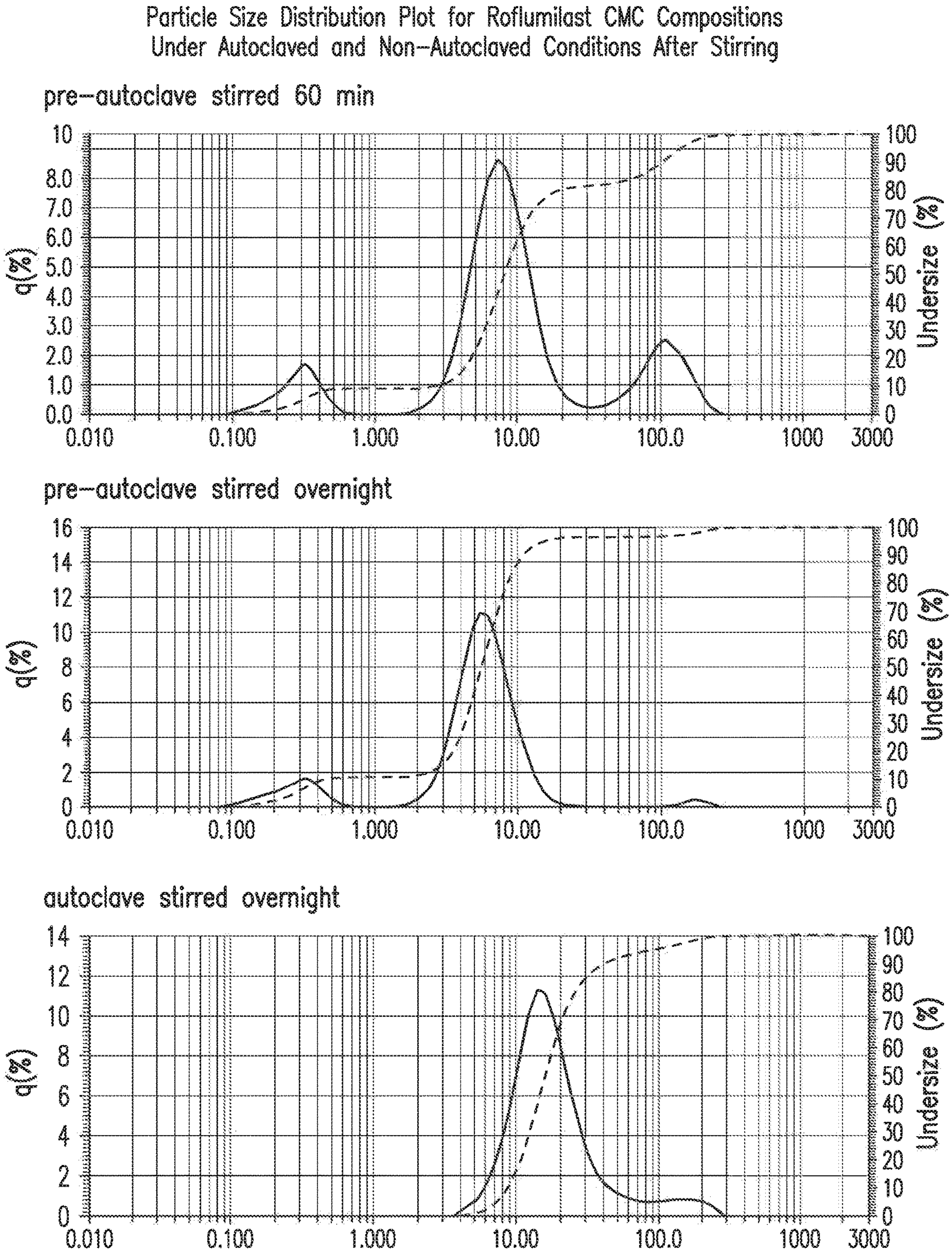

FIG. 12 is particle size distribution plots for an ophthalmic pharmaceutical composition comprising 0.10% roflumilast, 0.50% carboxymethyl cellulose, 0.1% polysorbate, 0.45% phosphate, and 0.05% citrate at a pH of 6.4-6.5, which compares non-autoclaved and autoclaved conditions with stirring.

Figure 13:
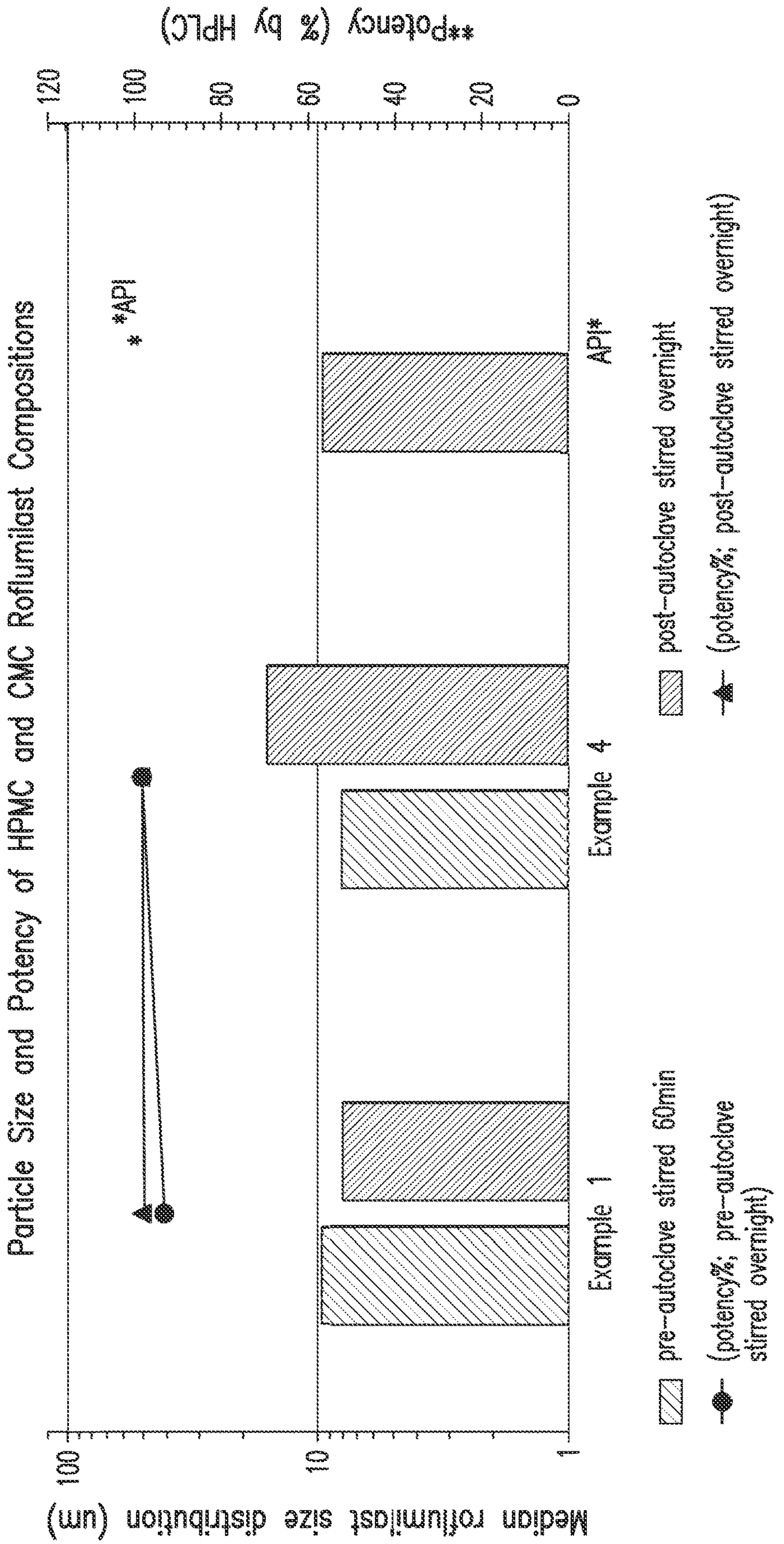

FIG. 13 is a plot comparing the median particle size and HPLC potency of exemplary ophthalmic pharmaceutical composition of roflumilast and roflumilast API.

Figure 14:
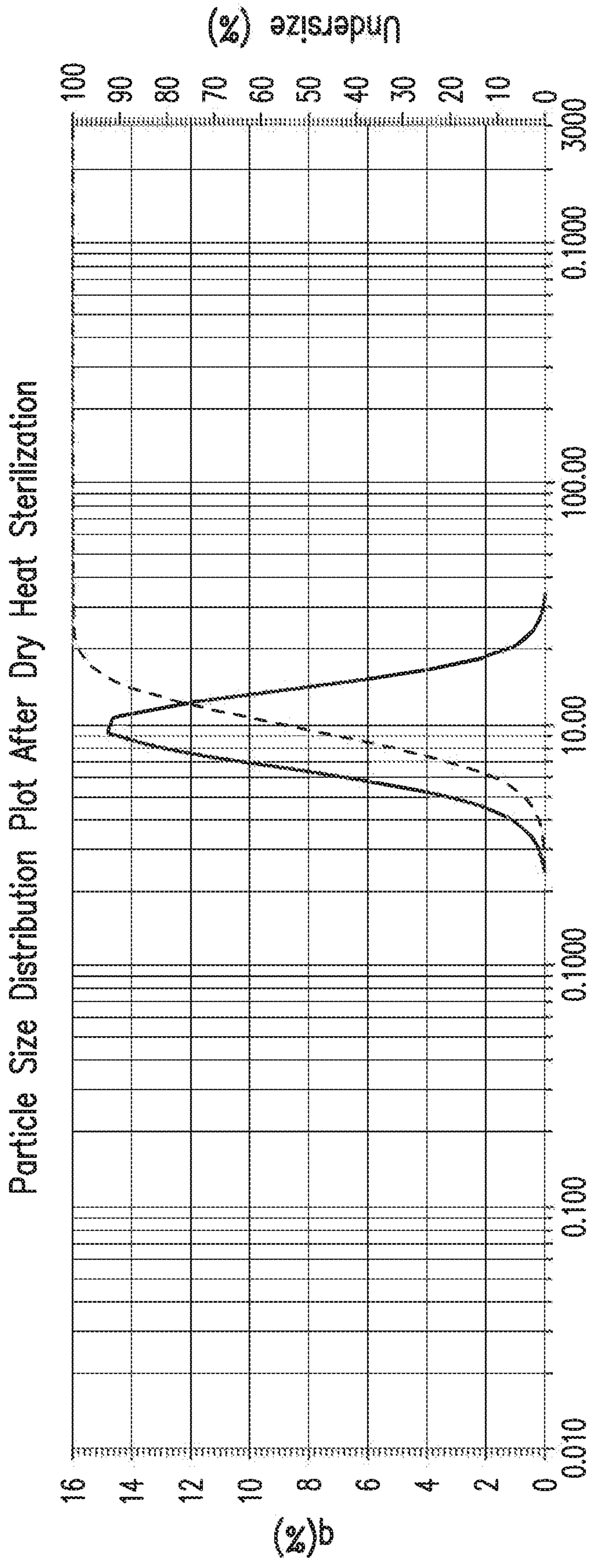

FIG. 14 provides a particle size distribution plot for bulk roflumilast API following dry heat sterilization.

Figure 15A:
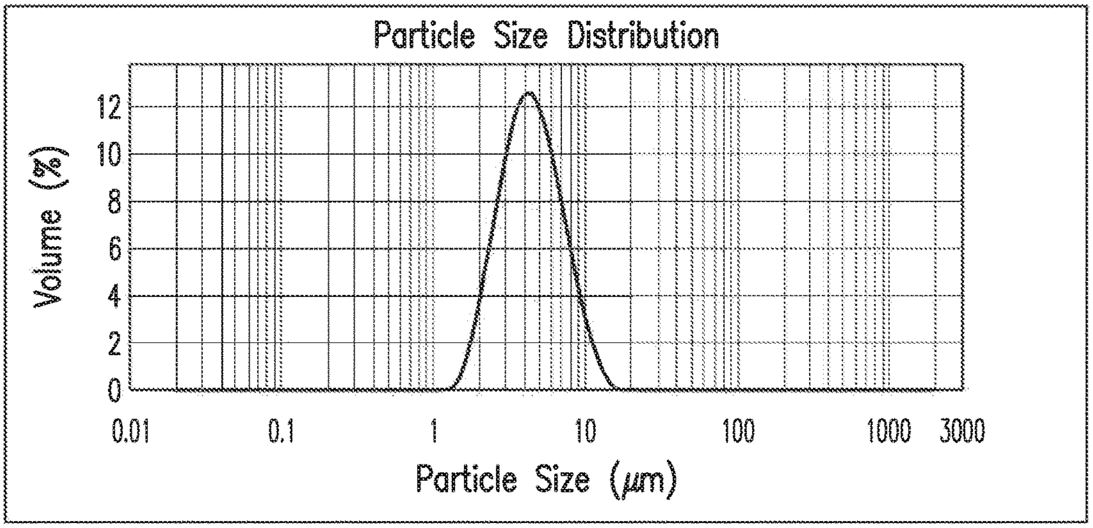

FIG. 15A provides particle size distribution plots for a roflumilast suspension pre-terminal gamma sterilization.

Figure 15B:
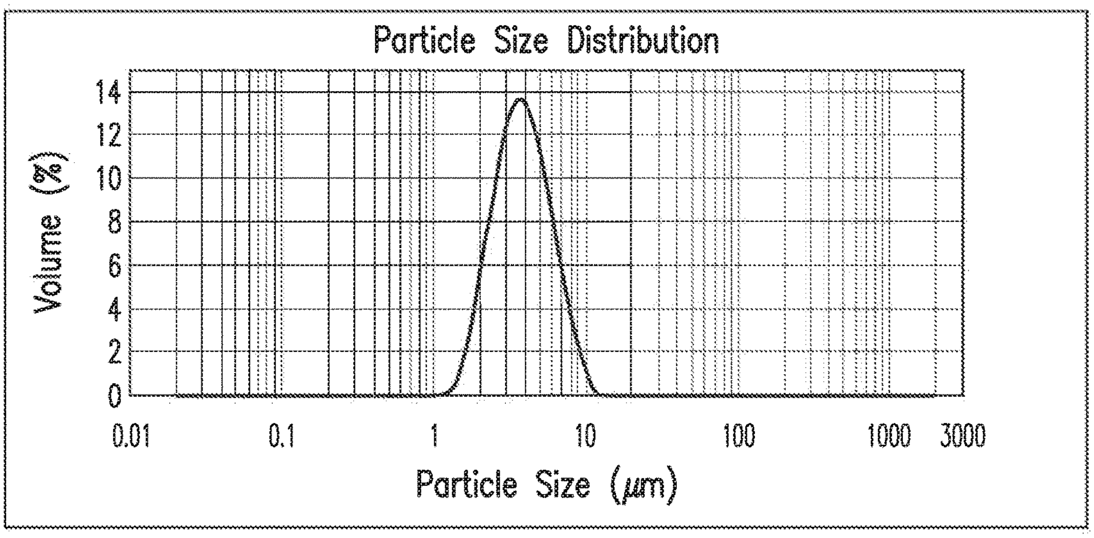

FIG. 15B provides a particle size distribution plot shortly after terminal gamma sterilization.

Figure 15C:
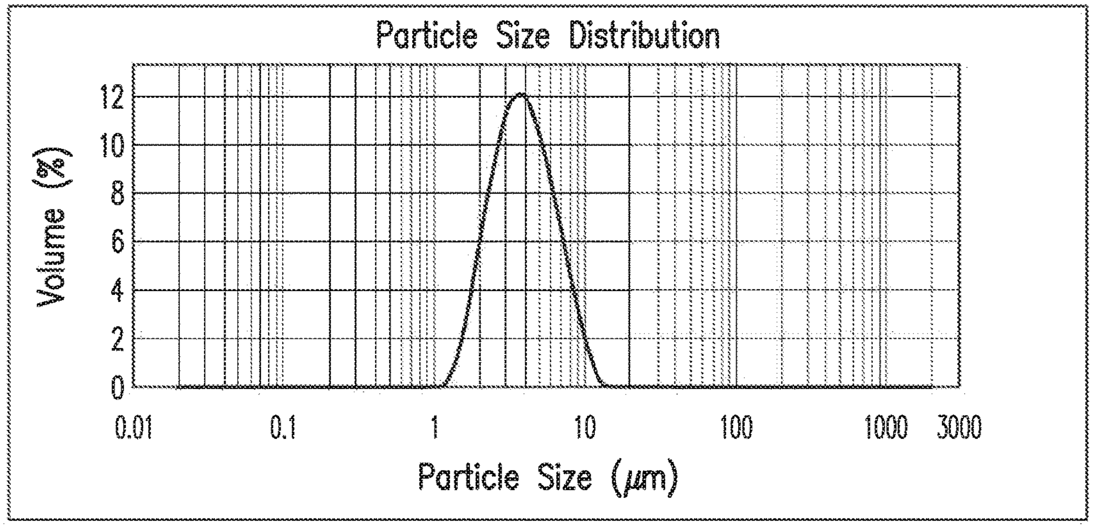

FIG. 15C provides a particle size distribution plot three days after terminal gamma sterilization.

Figure 15D:
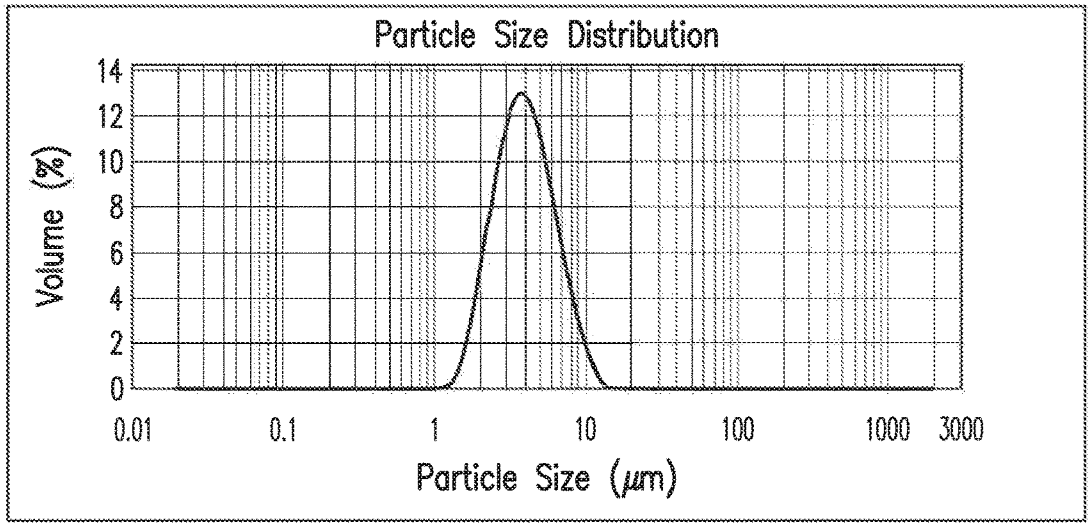

FIG. 15D provides a particle size distribution plot seven days after terminal gamma sterilization.

Figure 16A:
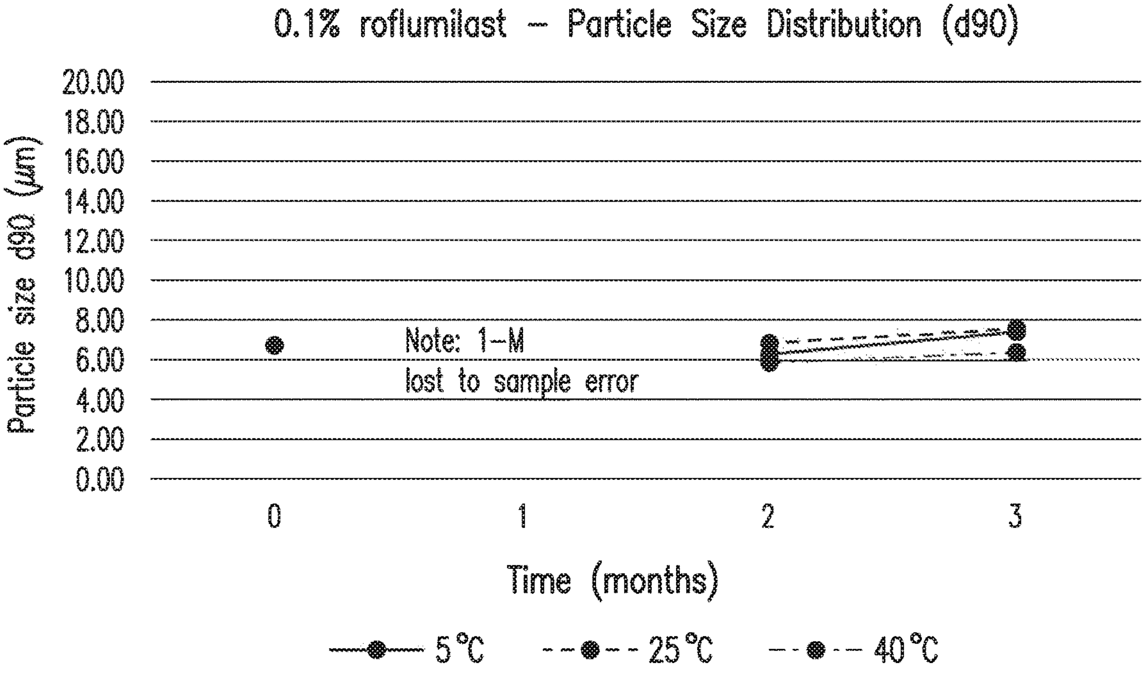

FIG. 16A provides particle size distribution plots for a 0.1% roflumilast suspension under different stability conditions (5° C., 25° C., and 40° C.) after terminal gamma sterilization.

Figure 16B:
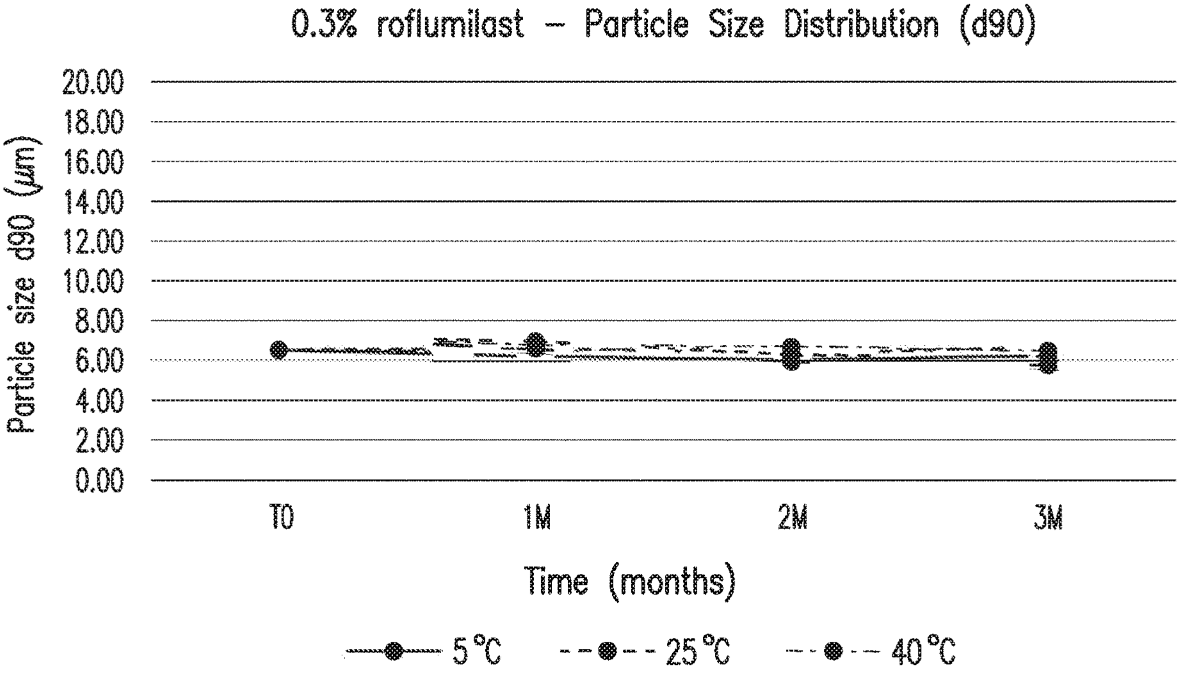

FIG. 16B provides particle size distribution plots for a 0.3% roflumilast suspension under different stability conditions (5° C., 25° C., and 40° C.) after terminal gamma sterilization.

Figure 16C:
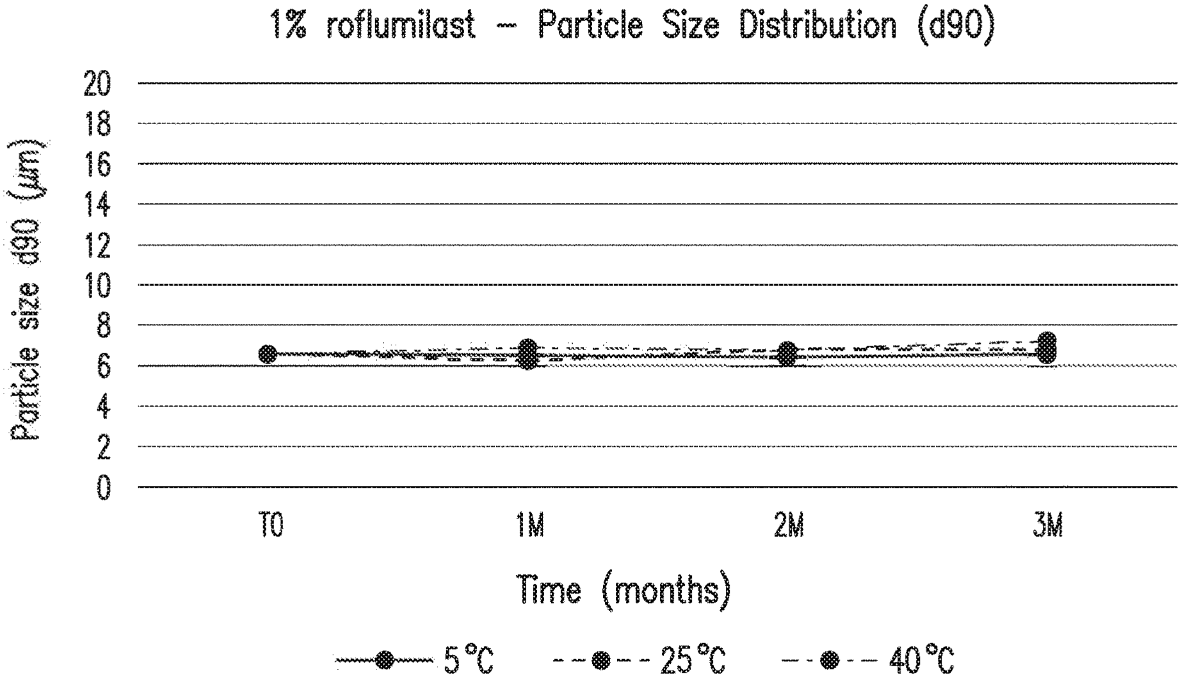

FIG. 16C provides particle size distribution plots for a 1.0% roflumilast suspension under different stability conditions (5° C., 25° C., and 40° C.) after terminal gamma sterilization.

Figure 17A:
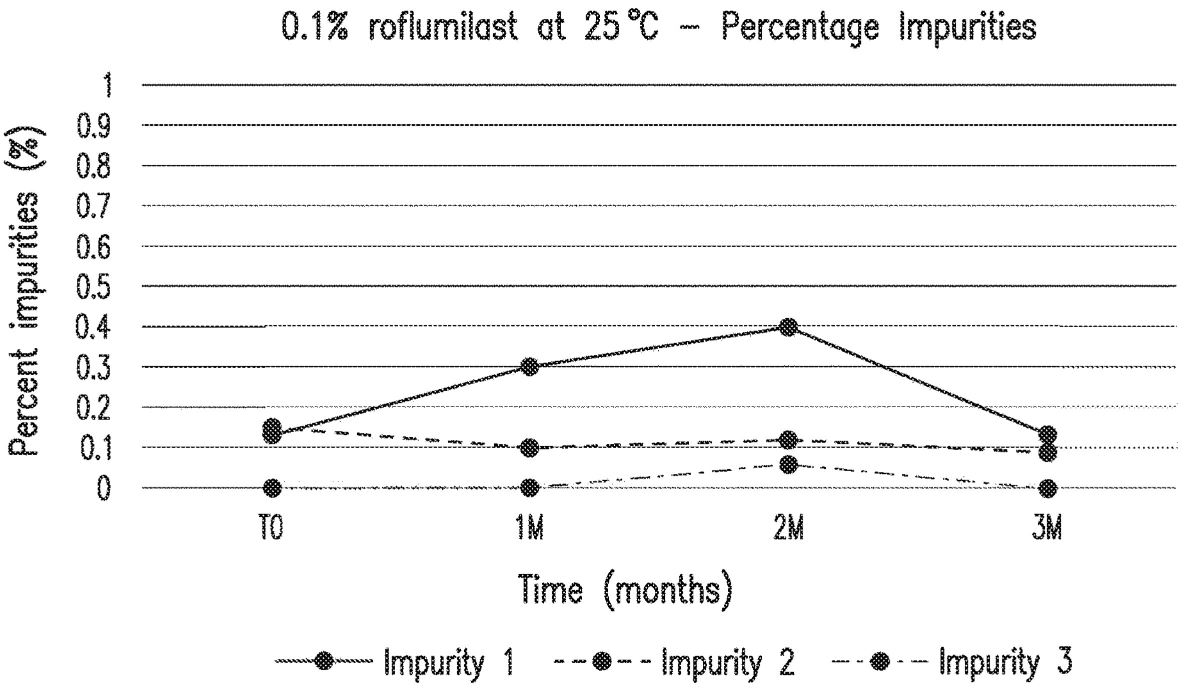

FIG. 17A provides the percentage of impurities for a 0.1% roflumilast suspension under different stability conditions (5° C., 25° C., and 40° C.) after terminal gamma sterilization.

Figure 17B:
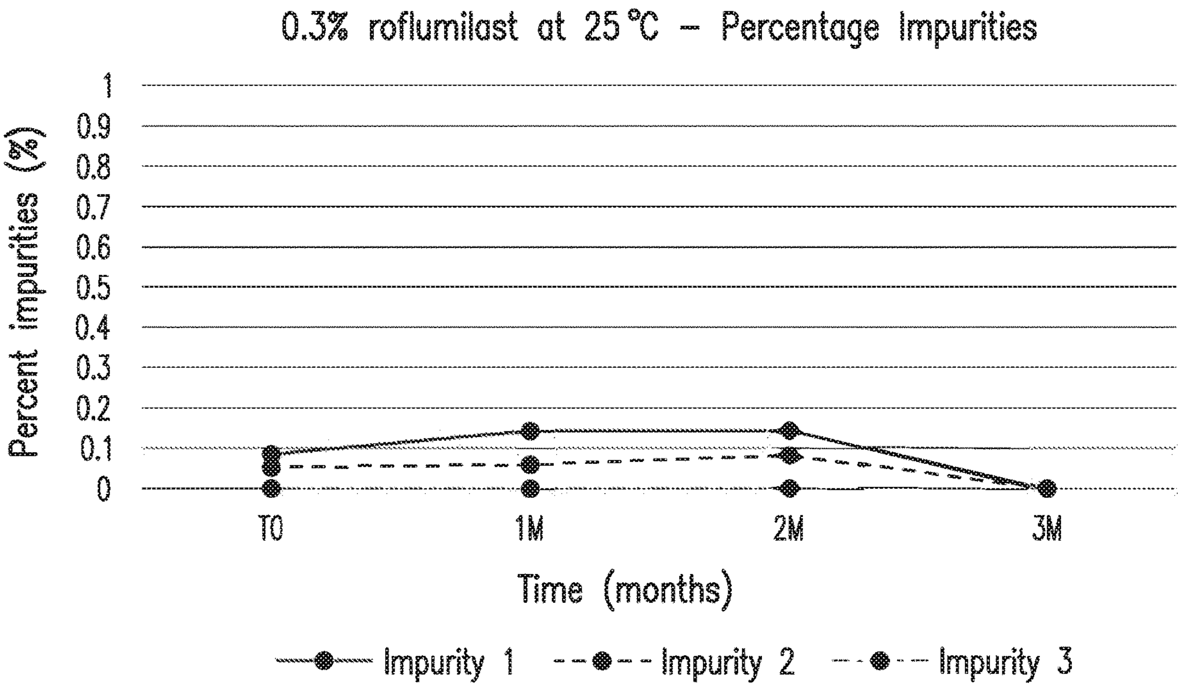

FIG. 17B provides the percentage of impurities for a 0.3% roflumilast suspension under different stability conditions (5° C., 25° C., and 40° C.) after terminal gamma sterilization.

Figure 17C:
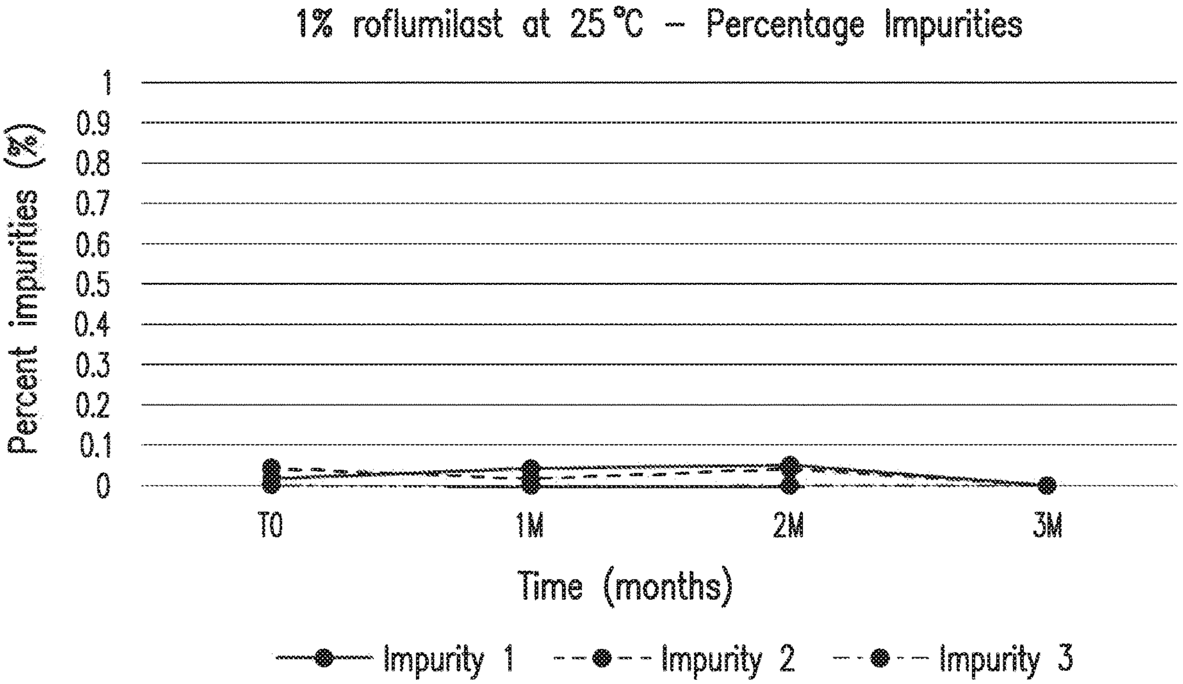

FIG. 17C provides the percentage of impurities for a 1.0% roflumilast suspension under different stability conditions (5° C., 25° C., and 40° C.) after terminal gamma sterilization.

DETAILED DESCRIPTION OF THE INVENTION

It is to be understood that the invention is not limited to the particular methodology, protocols, and reagents described herein as these may vary. It is also to be understood that the terminology used herein is for the purpose of describing particular embodiments only and is not intended to limit the scope of the present invention which will be limited only by the appended claims. Unless defined otherwise, all technical and scientific terms used herein have the same meanings as commonly understood by one of ordinary skill in the art to which this invention belongs.

All publications, patents and patent applications cited herein are hereby incorporated by reference in their entirety unless otherwise stated. Where the same term is defined in a publication, patent, or patent application and the present disclosure incorporated herein by reference, the definition in the present disclosure represents a controlling definition. For publications, patents and patent applications referenced to describe a particular type of compound, chemistry, etc., the portion relating to such compounds, chemistry, etc. is the portion of the literature incorporated herein by reference.

Note that as used herein, the singular forms "a," "an," and "the" include plural referents unless the context clearly dictates otherwise. Thus, for example, "active ingredient" includes a single ingredient and two or more different ingredients.

The term "about" when used in connection with a numerical value is meant to encompass numerical values within a range having a lower limit that is 5% smaller than the indicated numerical value and having an upper limit that is 5% larger than the indicated numerical value.

The term "effective" refers to an amount of a compound, agent, substance, formulation or composition that is of sufficient quantity to result in a decrease in severity of disease symptoms, an increase in frequency and duration of disease symptom-free periods, or a prevention of impairment or disability due to the disease affliction. The amount may be as a single dose or according to a multiple dose regimen, alone or in combination with other compounds, agents or substances. One of ordinary skill in the art would be able to determine such amounts based on such factors as a subject's size, the severity of a subject's symptoms, and the particular composition or route of administration selected.

"Pharmaceutically acceptable" means generally safe for administration to humans or animals. Preferably, a pharmaceutically acceptable component is one that has been approved by a regulatory agency of the Federal or a state government or listed in the U.S. Pharmacopeia, published by the United States Pharmacopeial Convention, Inc., Rockville Md., or other generally recognized pharmacopeia for use in animals, and more particularly in humans.

A "pharmaceutical composition" according to the invention may be present in the form of a composition, wherein the different active ingredients and diluents and/or carriers are admixed with each other, or may take the form of a combined preparation, where the active ingredients are present in partially or totally distinct form. An example for such a combination or combined preparation is a kit-of-parts.

The term "roflumilast" as used in this application refers to roflumilast, its salts, the N-oxide of roflumilast, and its salts, and other metabolites unless specified otherwise or unless it is clear in context that reference is to roflumilast itself.

As used herein, the terms "subject" "or patient" most preferably refers to a human being. The terms "subject" or "patient" may include any mammal that may benefit from the compounds described herein.

A "therapeutic amount" or "therapeutically effective amount" is an amount of a therapeutic agent sufficient to achieve the intended purpose. The effective amount of a given therapeutic agent will vary with factors such as the nature of the agent, the route of administration, the size of the subject to receive the therapeutic agent, and the purpose of the administration. The effective amount in each individual case may be determined empirically by a skilled artisan according to established methods in the art.

As used herein, "treat," "treating," or "treatment" of a disease or disorder means accomplishing one or more of the following: (a) reducing the severity and/or duration of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in patients that have previously had the disorder(s); and (e) limiting or preventing recurrence of symptoms in patients that were previously symptomatic for the disorder(s).

The present invention relates to stable ophthalmic pharmaceutical compositions of the phosphodiesterase-4 inhibitor, roflumilast. Roflumilast is a compound of the formula (I):

(I)

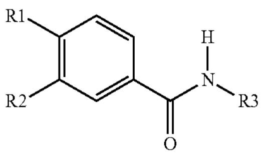

wherein R1 is difluoromethoxy, R2 is cyclopropylmethoxy and R3 is 3,5-dichloropyrid-4-yl.

Roflumilast has the chemical name N-(3,5-dichloropyrid-4-yl) cyclopropylmethoxy-4-difluoromethoxybenzamide. The N-oxide of roflumilast has the chemical name 3-cyclopropylmethoxy-4-difluoromethoxy-N-(3,5-dichloropyrid-4-yl 1-oxide)benzamide. Roflumilast and its synthesis, the use of roflumilast as a phosphodiesterase (PDE) 4 inhibitor, and roflumilast formulations, were described in U.S. Pat. No. 5,712,298, which is incorporated herein by reference. The ophthalmic pharmaceutical composition can include roflumilast as a free base or a pharmaceutically acceptable salt. Exemplary salts of roflumilast are salt described in paragraphs [0012] and [0013] of U.S. Patent Application Publication No. US 2006/0084684, the disclosure of which is incorporated herein by reference. In certain embodiments, the pharmaceutical composition comprises a metabolite of roflumilast, including the N-oxide of the pyridine residue of roflumilast or salts thereof, as an active ingredient.

In certain embodiments, the ophthalmic pharmaceutical composition can comprise roflumilast in a range from about 0.01% w/v to about 5.0% w/v, or from about 0.01% w/v to about 3.0% w/v, or from about 0.01% w/v to about 2.0% w/v, or from about 0.01% to about 1.0% w/v, or from about 0.01% to about 0.3% w/v. For example, the ophthalmic pharmaceutical comprises any of the following w/v percents of roflumilast: 0.01,%, 0.05%, 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 7%, 1.8%, 1.9%, 1.0%, 2.1%, 2.2%, 2.3%, 2.4%, 2.5%, 2.6%, 2.7%, 2.8%, 2.9%, 3.0%, etc.

In certain embodiments, the ophthalmic pharmaceutical composition can be a suspension, solution, eye drops, eye ointments, gels, creams, a spray, nasal spray, an injectable formulation (intravitreal, subconjunctival, sub-tenon, suprachoroidal or other injections), or an adsorbent implant, depot or adsorbent contact lens. In preferred embodiments, the pharmaceutical composition is a suspension, wherein the active ingredient (i.e., roflumilast) is suspended in a pharmaceutical carrier and/or excipients. In certain embodiments, the ophthalmic pharmaceutical composition of roflumilast comprises a viscosity agent, a surfactant, and a buffer. In certain embodiments, the ophthalmic pharmaceutical composition can include one or more additional excipients, including for example, a stabilizer, a preservative, a wetting agent, a diluting agent, a pH adjuster, a tonicity agent, or an absorption enhancer. In certain embodiments, the ophthalmic pharmaceutical composition can also be utilized for anterior or posterior ophthalmic situations in the form of an injection (intravitreal, suprachoroidal, or other), as a depot, an implantable adsorbent device for any ophthalmic or surrounding tissue placement, an in situ forming gel, or a drug/device combination, wherein the active ingredient (i.e., roflumilast) is suspended with one or more of the excipients above, for example a viscosity agent, a surfactant, or a buffer; with or without a device or inert depot compound.

In certain embodiments, the viscosity agent is at least one selected from the group consisting of hydroxypropyl methylcellulose (HPMC), hydroxyethylcellulose (HEC), polyvinyl pyrrolidione or povidone (PVP), carboxymethyl cellulose, hypromellose, methylcellulose, or polyvinyl alcohol (PVA). In certain embodiments, the viscosity agent is a dextran or gelatin. In addition, the viscosity agent can include a carbomer in certain embodiments, such as a carbomer copolymer Type A or a carbomer copolymer Type B including those marketed under the trade name Carbopol® by Lubrizol®. In certain embodiments, the ophthalmic pharmaceutical formulation can comprise a viscosity agent in a range from about 0.1% w/v to about 5.0% w/v, or from about 0.1% w/v to about 4.0% w/v, or from about 0.1% w/v to about 3.0% w/v, or from about 0.1% w/v to about 2.0% w/v, or from about 0.1% to about 1.0% w/v, or from about 0.1% to about 0.5% w/v. For example, the ophthalmic pharmaceutical comprises any of the following w/v percents of a viscosity agent: 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 7%, 1.8%, 1.9%, 1.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, etc.

In certain embodiments, the surfactant is at least one selected from the group consisting of polysorbates (including, polysorbate 20, polysorbate 40, polysorbate 60, and polysorbate 80) and tyloxapol. In certain embodiments, the ophthalmic pharmaceutical formulation can comprise a surfactant in a range from about 0.05% w/v to about 3.0% w/v, or from about 0.05% w/v to about 2.0% w/v, or from about 0.05% to about 1.0% w/v, or from about 0.1% to about 0.5% w/v. For example, the ophthalmic pharmaceutical comprises any of the following w/v percents of a surfactant: 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 7%, 1.8%, 1.9%, 1.0%, 2.1%, 2.2%, 2.3%, 2.4%, 2.5%, 2.6%, 2.7%, 2.8%, 2.9%, 3.0%, etc.

In certain embodiments, the buffer is at least one selected from the group consisting of citrate, phosphate, Tris-HCl (Tris), acetate, and borate buffers. In certain embodiments, the ophthalmic pharmaceutical formulation can comprise a buffer in a range from about 0.5% w/v to about 7.5% w/v, or from about 0.5% w/v to about 5.0% w/v, or from about 0.5% to about 3.0% w/v, or from about 0.5% w/v to about 2.0% w/v, or from about 0.5% to about 1.0% w/v. For example, the ophthalmic pharmaceutical comprises any of the following w/v percents of a buffer: 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 7%, 1.8%, 1.9%, 1.0%, 2.1%, 2.2%, 2.3%, 2.4%, 2.5%, 2.6%, 2.7%, 2.8%, 2.9%, 3.0%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, etc.

In certain embodiments, the ophthalmic pharmaceutical formulation is an ointment. The ointment can include inactive ingredients selected from the group consisting of petrolatum, mineral oil. In such embodiments, the ophthalmic pharmaceutical formulation can comprise a therapeutically effective amount of roflumilast, petrolatum, and mineral oil. In certain embodiments, the composition comprises from about 0.1% w/v to about 3.0% w/v, or from about 0.1% w/v to about 2.0% w/v, or from about 0.1% to about 1.0% w/v of roflumilast. In certain embodiments, the composition comprises from about 75% to about 85% w/w of petrolatum, or more preferably from about 75% to about 80% w/w of petrolatum. In certain embodiments, the composition comprises from about 15% to about 25% w/w mineral oil, or more preferably from about 15% to about 20% w/w of mineral oil. The ointment can provide benefits relative to suspensions, including for example, increasing contact time and increasing the soluble drug concentration in the dosing system, which can be important for a water-insoluble drug like roflumilast.

The inventors of the subject application have identified that roflumilast undergoes hydrolysis at low potencies in certain ophthalmic pharmaceutical compositions and under certain standard sterile manufacturing processes. The inventors of the subject application have discovered the ophthalmic pharmaceutical compositions of the present invention can reduce the rate of hydrolysis. In certain embodiments, the pH of the ophthalmic pharmaceutical compositions is between about 6.0 and about 6.7 to reduce the rate of hydrolysis of roflumilast. In preferred embodiments, the pH of the ophthalmic pharmaceutical composition is between about 6.2 and about 6.7, and more preferably between about 6.3 to about 6.6. In preferred embodiments, the osmolality of the ophthalmic pharmaceutical composition is about 270 mOsm/kg to 330 mOsm/kg, more preferably about 270 mOsm/kg to about 300 mOsm/kg, and even more preferably 270 mOsm/kg to 280 mOsm/kg.

The ophthalmic pharmaceutical compositions of the present invention are stable and exhibit a particle size distribution suitable for ophthalmic delivery. Particle size of the ophthalmic pharmaceutical composition for suspensions can be assessed using laser diffraction methods. Laser diffraction is recognized by standards and guidance agencies including ISO and ASTM and is widely used to determine particle size distributions. In conducting the assessment, the sample is passed through a laser beam, which results in laser light scattered at a range of angles. Detectors placed at fixed angles measure the intensity of light scattered at that position. A mathematical model is then applied to generate a particle size distribution.

In particle size determinations, the median value is defined as the value where half of the population resides above this point, and half resides below this point. For particle size distributions the median is called the D50. The D50 is the size that splits the distribution with half above and half below this diameter. The distribution width may also be characterized by citing one, two or three values on the x-axis, typically some combination of the D10, D50, and D90. The D50 (or the median), as discussed above, refers to the diameter wherein half of the population lies below this value. Similarly, 90 percent of the distribution lies below the D90, and 10 percent of the population lies below the D10.

In certain embodiments of the present invention, the ophthalmic pharmaceutical composition exhibits a particle size distribution characterized by a d90 value of less than or equal to about 50 μm prior to preferential processing. In certain embodiments, the ophthalmic pharmaceutical composition exhibits a particle size distribution characterized by a d90 value of from about 5 μm to about 25 μm. In certain embodiments, the pharmaceutical compositions exhibits a particle size distribution characterized by a d90 value of from about 5 μm to about 15 μm. In preferred embodiments, the pharmaceutical compositions exhibit a particle size distribution characterized by a d90 value of less than or equal to 10 μm.

The inventors of the subject application have identified that roflumilast in combination with multiple viscosity agents undergoes particle size growth and aggregation in certain heat transferring ophthalmic pharmaceutical manufacturing processes designed to sterilize a formulation. The inventors of the subject application have discovered certain methods of avoiding this aggregate causing heat transfer during sterile processing of the roflumilast in the same vessel as the inactive ingredients including the excipients, surfactants, etc., which can reduce the rate of particle size growth and aggregation while maintaining product potency. Mixing both sterile API with sterile inactives reduces particle aggregation by reducing the need for additional energy inputs like autoclaving, which can cause particle aggregation. In certain embodiments, dry heat sterilization at a temperature less than the melting point of roflumilast, gamma radiation, or other methods of sterilization of API can be used to sterilize the roflumilast while standard autoclaving can be used to sterilize the inactives before creating the final mixed formulation for an ophthalmic pharmaceutical composition which is optimized in potency, purity, and particle size, ideal for use in the eye. In certain embodiments, gamma radiation or other terminal product sterilization methods can be used to sterilize the drug product to ensure the final product is sterilized in packaging, as a way to further ensure sterility-assurance and patient safety. The inventors of the subject application have discovered certain methods of terminal sterilization which avoid product degradation or further creation of impurities. In certain embodiments, the packaged ophthalmic pharmaceutical composition can be characterized by a retained potency of greater than 99% of the original value of active substances. In certain embodiments, the retained potency is greater than 99.1%, 99.2%, 99.3%, 99.4%, 99.5%, 99.6%, 99.7%, or 99.8% of the original value of active substances.

In certain embodiments of the present invention, a method of manufacturing an ophthalmic pharmaceutical composition of roflumilast is provided. The pharmaceutical composition can include the pharmaceutical compositions described above. The method can include sterilizing the roflumilast using a form of dry heat or low level radiation sterilization. The sterilization can be achieved by dry heat sterilization at a temperature less than the melting point of roflumilast (approximately 159.7° C.), gamma radiation, or other methods of sterilization. The method can further include sterilizing at least one inactive ingredient selected from the group consisting of a viscosity agent, surfactant, and buffer using standard autoclaving. The method can further include mixing the sterilized roflumilast with the sterilized inactive ingredient to prepare a stable ophthalmic pharmaceutical composition of roflumilast. In certain embodiments, the pharmaceutical composition that is prepared is a suspension.

In certain embodiments, the method can further include subjecting the stable ophthalmic pharmaceutical composition of roflumilast to clarity filtration to further mitigate particle size aggregation and to create an optimal suspension. The clarity filtration can be used to produce a stable ophthalmic pharmaceutical composition of roflumilast, wherein the pharmaceutical composition has a particle size distribution characterized by a d90 value of less than or equal to 10 μm, further differentiated for use in the eye, particularly in patients who may have sensitivity to existing ophthalmic agents. The different formulations can react differently to the filtration process due to the differences in creation of aggregates in some formulations.

In certain embodiments of the present invention, a method of manufacturing an ophthalmic pharmaceutical composition of roflumilast is provided. The pharmaceutical composition can include the pharmaceutical compositions described above. The method can include preparation of the pharmaceutical compositions under GLP or GMP conditions, followed by low level radiation sterilization of the final drug product in terminal packaging, called terminal sterilization. The sterilization can be achieved by gamma radiation at a low or medium dose (e.g., low dose at 18-25 Kilograys or medium dose at 25-28 Kilograys). Typical radiation dose mapping procedure involves placing a tray with samples on a stand located centrally in a gamma-ray generating chamber. At least two dosimeters are placed on the samples, one over and other under tray. Minimum (Dmin) and maximum dose (Dmax) estimations are conducted, in addition to a separate monitoring dosimeter (Dmon) usually placed above the sample tray. Dosimeter placement and measurements are typically repeated according to an ISO 11137-3. Dmin, Dmax, and Dmon are calculated as average of performed measurements. This method of sterilization is preferred for patient use because both the product and the packaging are sterilized together, resulting in further certainty that the product will have the needed sterility for single-use clinical application. In certain embodiments, the pharmaceutical composition that is prepared is a suspension.

The ophthalmic pharmaceutical compositions of the present invention can be administered directly to the ocular surface of a patient, and the teachings herein can also be used to create injectable or implantable formulations for ocular surface, anterior, or posterior ophthalmic use. The pharmaceutical composition of roflumilast can be administered to the eye of a patient having an eye disorder or eye condition. The ophthalmic pharmaceutical compositions of the present invention applied to ocular surface disease can be used to treat eye disorders without the need for invasive techniques, which are sometimes required to deliver drug to the anterior or posterior of the eye. Examples of ocular surface eye disorders that can be treated by the methods disclosed herein can include: Post-operative pain and inflammation from Cataract or other ocular Surgery or Laser Therapy, post corneal refractive surgery haze, post-operative full or partial thickness corneal transplantation, dry eye syndrome including Sjogren's or other autoimmune or inflammatory dry eye disease, evaporative or dessicative dry eye disease, ocular graft vs host disease, ocular rosacea, allergic conjunctivitis or keratoconjunctivitis, atopic conjunctivitis, vernal keratoconjunctivitis, keratitis, herpetic keratitis including herpetic stromal keratitis, herpetic blepharitis or conjunctivitis, zoster related inflammation, inflammation secondary to other infectious agents such as bacterial, viral, or fungal infections, inflammation secondary to ocular chemical burns, ocular Stevens-Johnson syndrome/tens, uveitis including uveitis of juvenile idiopathic arthritis, seborrheic or other forms of blepharitis, limbal stem cell deficiency, meibomian gland dysfunction, episcleritis, pingueculitis, pterygia, phlyctenulosis, staphylococcal hypersensitivity, Mooren's ulcer, endotheleitis, superior limbic keratoconjunctivitis, or other ocular conditions traditionally treated with steroids where patients are contra-indicated due to a history of intra-ocular pressure, wound healing, fungal infections, etc. Certain embodiments which could use these formulations as an injection of multiple types or a depot could be used to treat anterior or posterior inflammatory ocular disease such as anterior- pan- and posterior uveitis (infectious or non-infectious), juvenile idiopathic arthritis associated uveitis, posterior complications of Bechet's disease, ocular graft vs host disease, Stevens-Johnson syndrome, diabetic retinopathy, diabetic macular edema, geographic atrophy, dry or wet age-related macular degeneration, retinal vein occlusion, retinal vasculitis (drug related/iatrogenic, non-infectious/sterile, or idiopathic), endophthalmitis, retinitis, choroiditis, anterior or posterior sclertis/episcleritis, endothelial keratitis (bacterial, viral, fungal, or non-infectious in nature), and other inflammatory diseases of the anterior and posterior tissues of the eye or ocular complications of other inflammatory or autoimmune diseases. Injections may also be used post-surgically to treat pain and inflammation of cataract, LASIK, full or partial thickness keratoplasty, glaucoma-related surgical procedures, inflammation related to gene or cell therapy instillation, or other surgical conditions and procedures where inflammation would be a concern. The eye disorders treatable by the methods described herein can be acute or chronic. In certain embodiments, the method is used to treat a patient having an inflammatory disorder of the eye. In certain embodiments, the inflammatory disorder can be one of the above-identified disorders.

In certain embodiments, the pharmaceutical composition is administered as a regimen, such as at regular intervals. For example, a pharmaceutical composition can be administered directly to the ocular surface as a drop or ointment once daily, twice daily, thrice daily, four times daily, once per week, twice per week, three times per week, or four times per week, monthly, or as needed (PRN). In certain embodiments, the pharmaceutical composition can be administered as part of a maintenance dose or titrating dose regimen. The pharmaceutical composition can be administered for a prescribed period of time. For example, a pharmaceutical composition can be administered for a period of about two days to at least about six weeks, or until an improvement in the eye condition or disease is observed. Exemplary periods of time for the treatment regimen include one week, two weeks, one month, six weeks, two months, three months, four months, five months, six months, seven months, eight months, nine months, or one year. For example, a pharmaceutical composition can be administered as an injection or as an implantable device, depot, or adsorbable device could be administered once per week, once per month, once every 2, 3, 4, 5, 6, 7, 8, 9, 10, 11, 12, 13, 14, 15, 16 weeks, once per quarter, once every sixth months, as needed (PRN), per physician direction, or per some clinical criteria such as treat and extend or other criteria. The pharmaceutical composition can be administered as an ongoing treatment with no end.

The following examples illustrate certain embodiments of the invention without limitation.

EXAMPLES

While various embodiments have been described herein, it should be understood that they have been presented by way of example only, and not limitation. Thus, the breadth and scope of the present disclosure should not be limited by any of the described exemplary embodiments. Moreover, any combination of the above-described elements in all possible variations thereof is encompassed by the disclosure unless otherwise indicated herein or otherwise clearly contradicted by context.

Nine ophthalmic pharmaceutical compositions comprising roflumilast were prepared as set forth in Examples 1—including different pharmaceutical compositions of 0.1% roflumilast suspensions, Examples 5-6 including different pharmaceutical compositions of ointments, and Example 7-9 including different pharmaceutical compositions including range of concentrations of roflumilast in the same pharmaceutical composition.

Example 1

Figure 1:
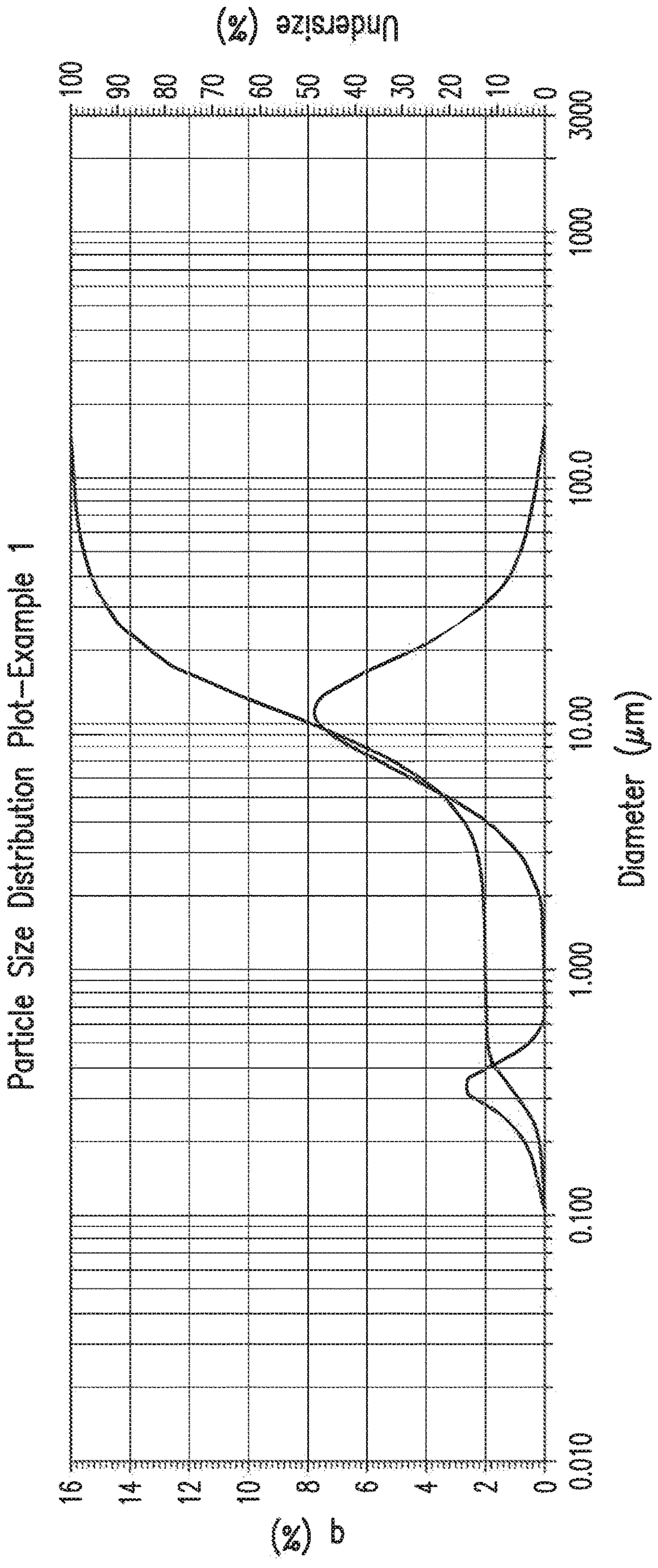
FIG. 1 is a particle size distribution plot for an ophthalmic pharmaceutical composition comprising 0.10% roflumilast, 0.30% hydroxypropyl methylcellulose, 0.1% polysorbate, 0.45% phosphate, and 0.05% citrate, post autoclaving and sonication of the formulation.

The ophthalmic pharmaceutical composition comprising roflumilast set forth in Table 1 was prepared. FIG. 1 provides a particle size distribution plot post autoclaving and sonication of the formulation.

TABLE 1

| Ophthalmic Pharmaceutical Suspension of Roflumilast | |
|---|---|
| Ingredient | % w/v |
| Roflumilast | 0.1% w/v |
| Hydroxypropyl methylcellulose | 0.3% w/v |
| Polysorbate 80 | 0.1% w/v |
| Phosphate/Citrate Buffer | 0.45%/0.05% w/v |
| Water for injection | q.s. ad 1.0 mL |

Example 2

Figure 2:
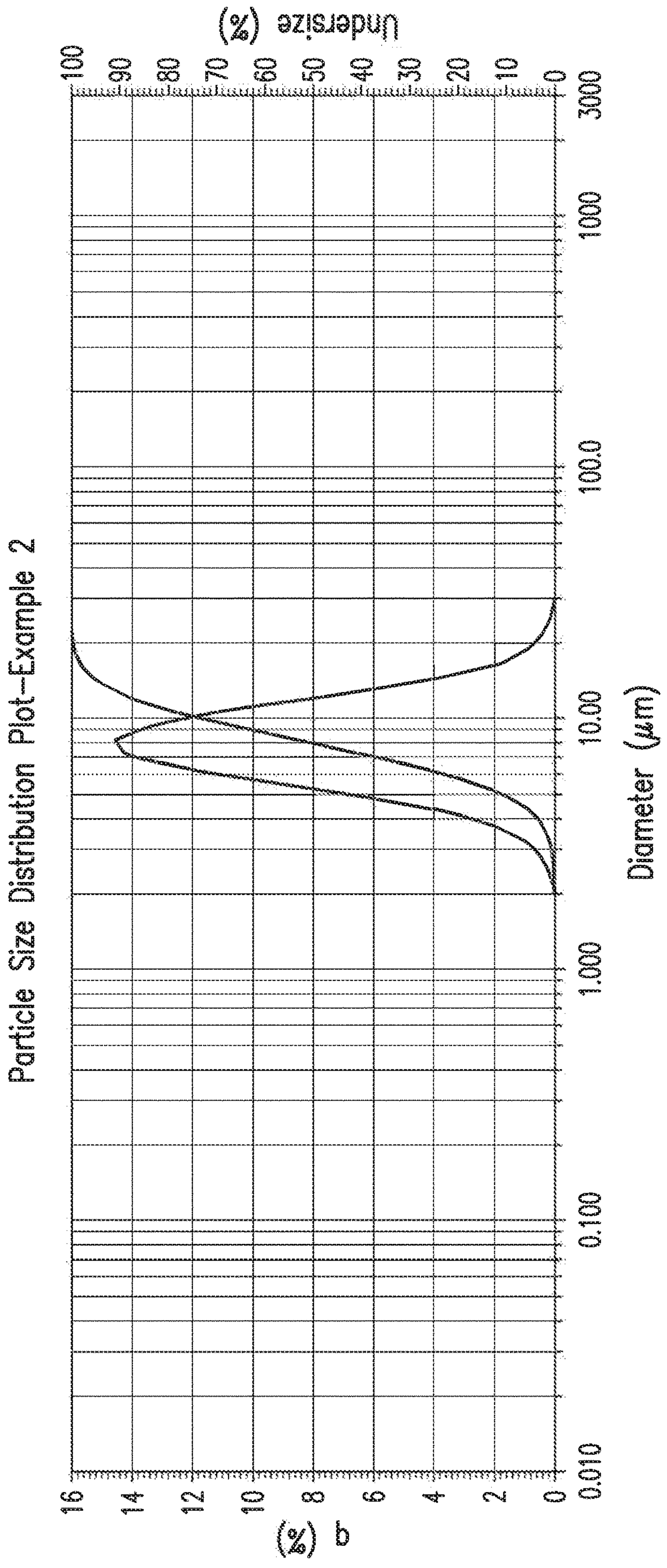
FIG. 2 is a particle size distribution plot for an ophthalmic pharmaceutical composition comprising 0.10% roflumilast, 0.35% hydroxyethyl cellulose, 0.1% polysorbate, 0.45% phosphate, and 0.05% citrate, post autoclaving and sonication of the formulation.

The ophthalmic pharmaceutical compositions comprising roflumilast set forth in Table 2 was prepared. FIG. 2 provides a particle size distribution plot post autoclaving and sonication of the formulation.

TABLE 2

| Ophthalmic Pharmaceutical Suspension of Roflumilast | |
|---|---|
| Ingredient | % w/v |
| Roflumilast | 0.1% w/v |
| Hydroxyethyl cellulose | 0.35% w/v |
| Polysorbate 80 | 0.1% w/v |
| Phosphate/Citrate Buffer | 0.45%/0.05% |
| Water for injection | q.s. ad 1.0 mL |

Example 3

Figure 3:
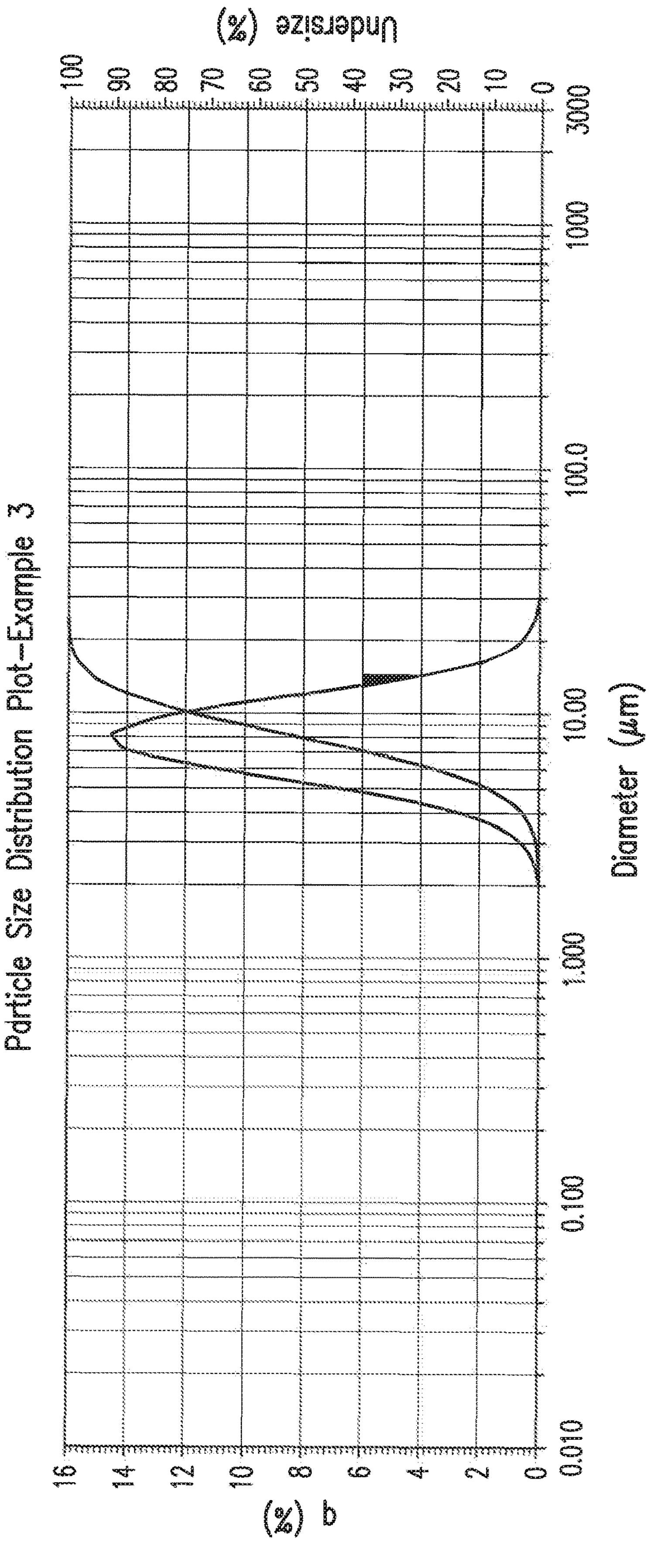
FIG. 3 is a particle size distribution plot for an ophthalmic pharmaceutical composition comprising 0.10% roflumilast, 0.60% polyvinylpyrrolidone, 0.3% tyloxapol, 0.45% phosphate, and 0.05% citrate, post autoclaving and sonication of the formulation.

The ophthalmic pharmaceutical composition comprising roflumilast set forth in Table 3 was prepared. FIG. 3 provides a particle size distribution plot post autoclaving and sonication of the formulation.

TABLE 3

| Ophthalmic Pharmaceutical Suspension of Roflumilast | |
|---|---|
| Ingredient | % w/v |
| Roflumilast | 0.1% w/v |
| Polyvinylpyrrolidone | 0.6% w/v |
| Tyloxapol | 0.3% w/v |
| Phosphate/Citrate Buffer | 0.45%/0.05% |
| Water for injection | q.s. ad 1.0 mL |

Example 4

Figure 4:
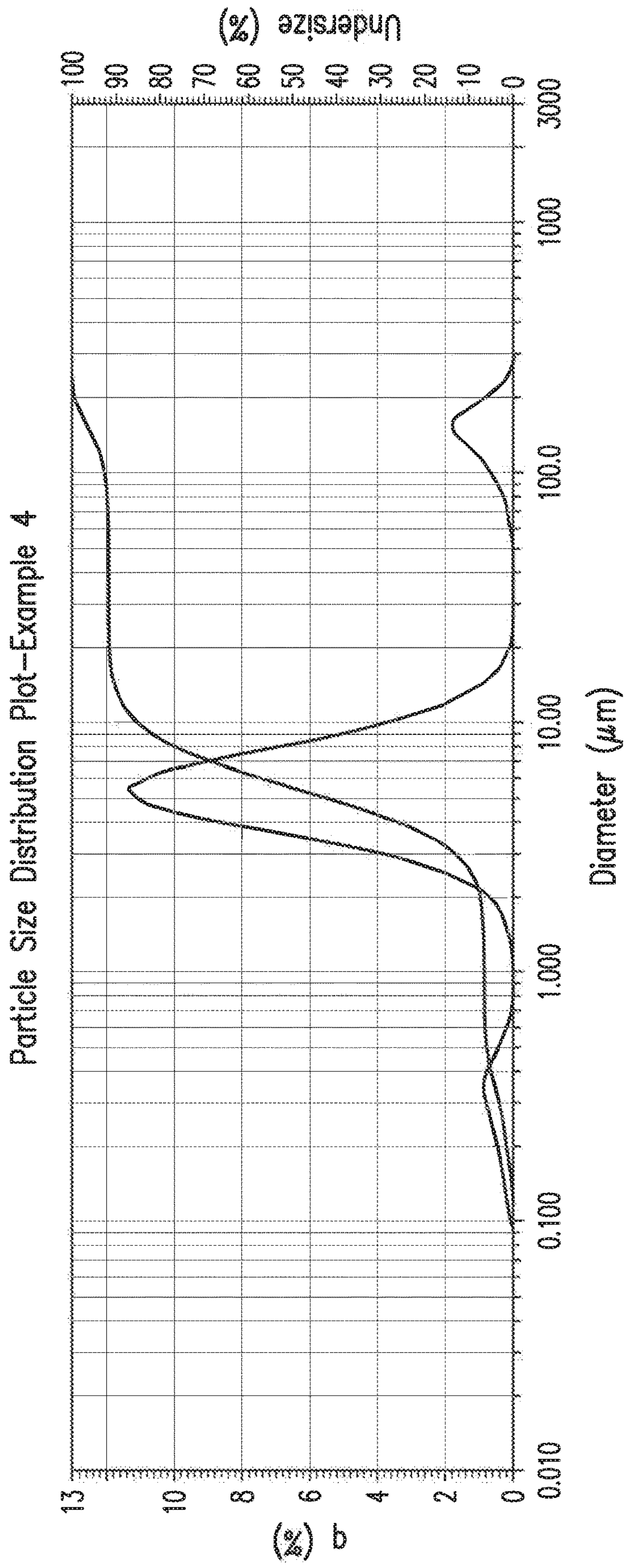
FIG. 4 is a particle size distribution plot for an ophthalmic pharmaceutical composition comprising 0.10% roflumilast, 0.50% carboxymethyl cellulose, 0.1% polysorbate, 0.45% phosphate, and 0.05% citrate, post autoclaving and sonication of the formulation.

The ophthalmic pharmaceutical composition comprising roflumilast set forth in Table 4 was prepared. FIG. 4 provides a particle size distribution plot post autoclaving and sonication of the formulation.

TABLE 4

| Ophthalmic Pharmaceutical Suspension of Roflumilast | |
|---|---|
| Ingredient | % w/v |
| Roflumilast | 0.1% w/v |
| Carboxymethyl cellulose | 0.5% w/v |
| Polysorbate 80 | 0.1% w/v |
| Phosphate/Citrate Buffer | 0.45%/0.05% |
| Water for injection | q.s. ad 1.0 mL |

Examples 5 and 6

The ophthalmic pharmaceutical ointments comprising roflumilast set forth in Table 5 was prepared.

TABLE 5

| Ophthalmic Pharmaceutical Ointment of Roflumilast | | |
|---|---|---|
| Ingredient | Example 5 (% w/w) | Example 6 (% w/w) |
| Roflumilast | 0.1% w/w | 1% w/w |
| Mineral oil | 79.7% w/w | 20% w/w |
| Petrolatum | 20.2% w/w | 79% w/w |

Example 7-9

The ophthalmic pharmaceutical suspensions comprising roflumilast in suspension at different concentrations set forth in Table 6 were prepared. The formulations were prepared with the same excipients set forth in Examples 1 and 3 but with different concentrations of roflumilast.

TABLE 6

Ophthalmic Pharmaceutical Suspensions of Roflumilast at Different Concentrations

| Ingredient | Example 7 (% w/w) | Example 8 (% w/w) | Example 9 (% w/w) |
|---|---|---|---|
| Roflumilast | 0.1% w/w | 0.3% w/w | 1% w/w |

Example 10

Figure 5A:
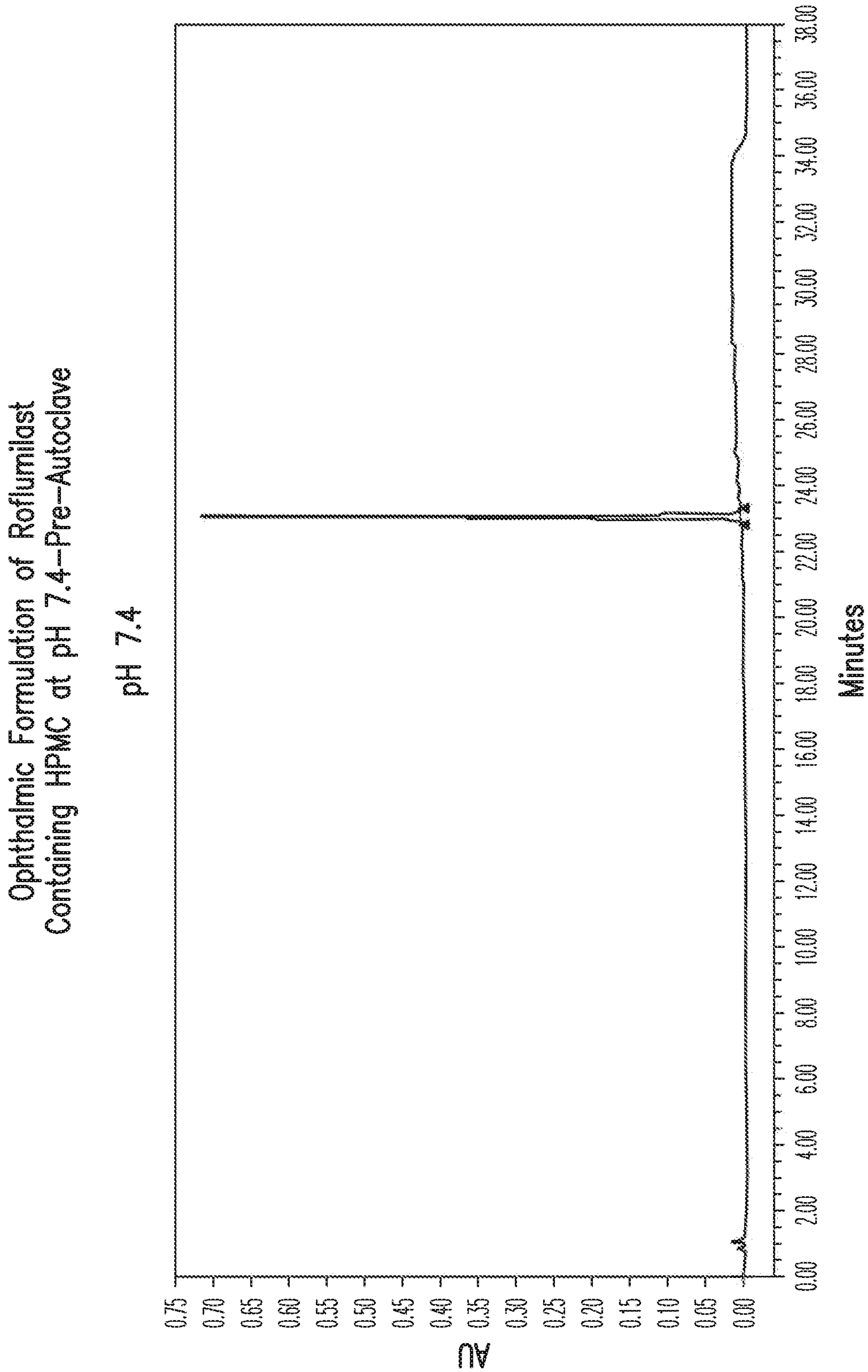
FIG. 5A is an HPLC chromatogram for an exemplary ophthalmic pharmaceutical composition comprising 0.10% roflumilast, 0.30% hydroxypropyl methylcellulose, 0.1% polysorbate, 0.45% phosphate, and 0.05% citrate at a pH of 7.4 under pre-autoclave conditions.
Figure 5B:
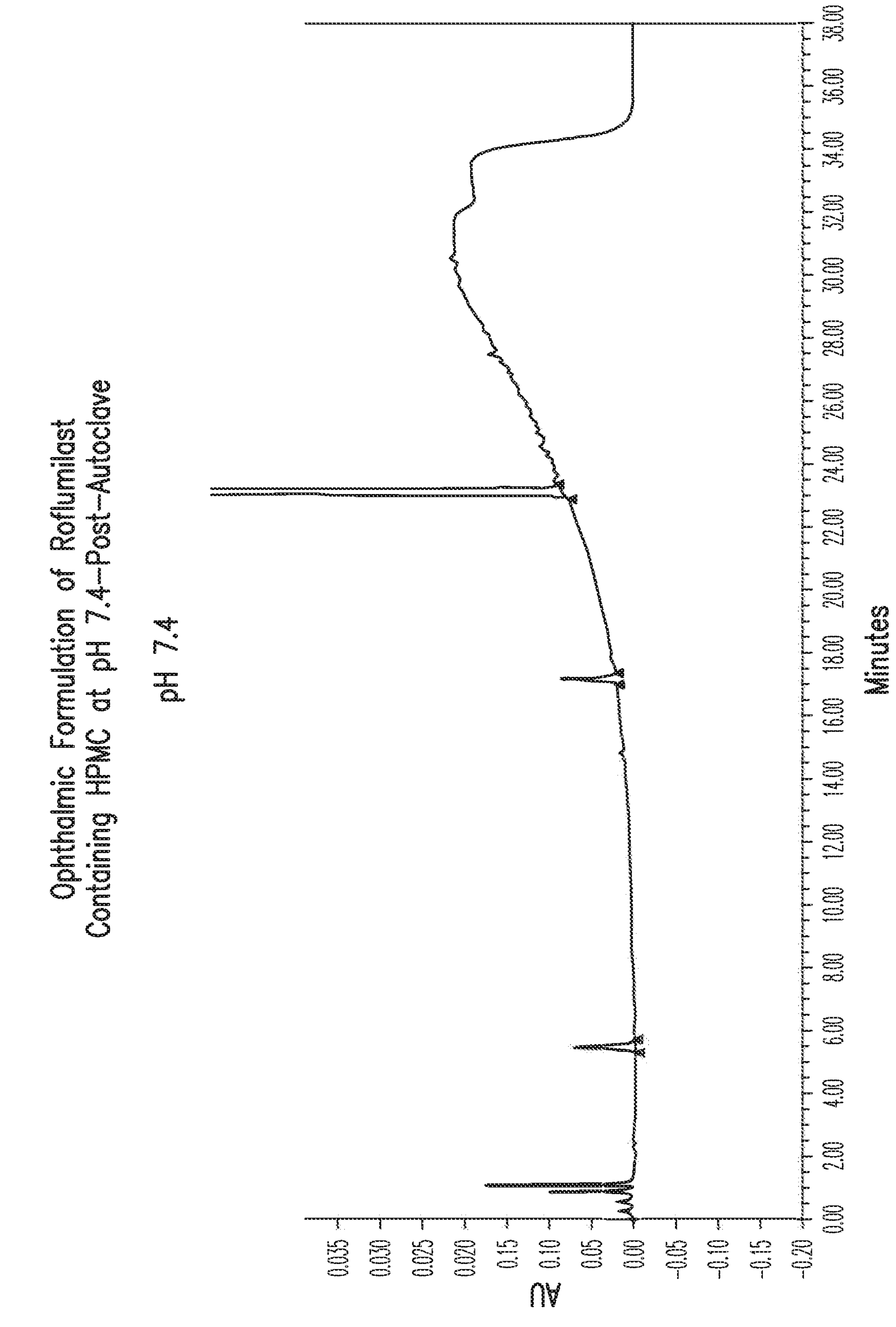
FIG. 5B is an HPLC chromatogram for an ophthalmic pharmaceutical composition comprising 0.10% roflumilast, 0.30% hydroxypropyl methylcellulose, 0.1% polysorbate, 0.45% phosphate, and 0.05% citrate at a pH of 7.4 under post-autoclave conditions.
Figure 5C:
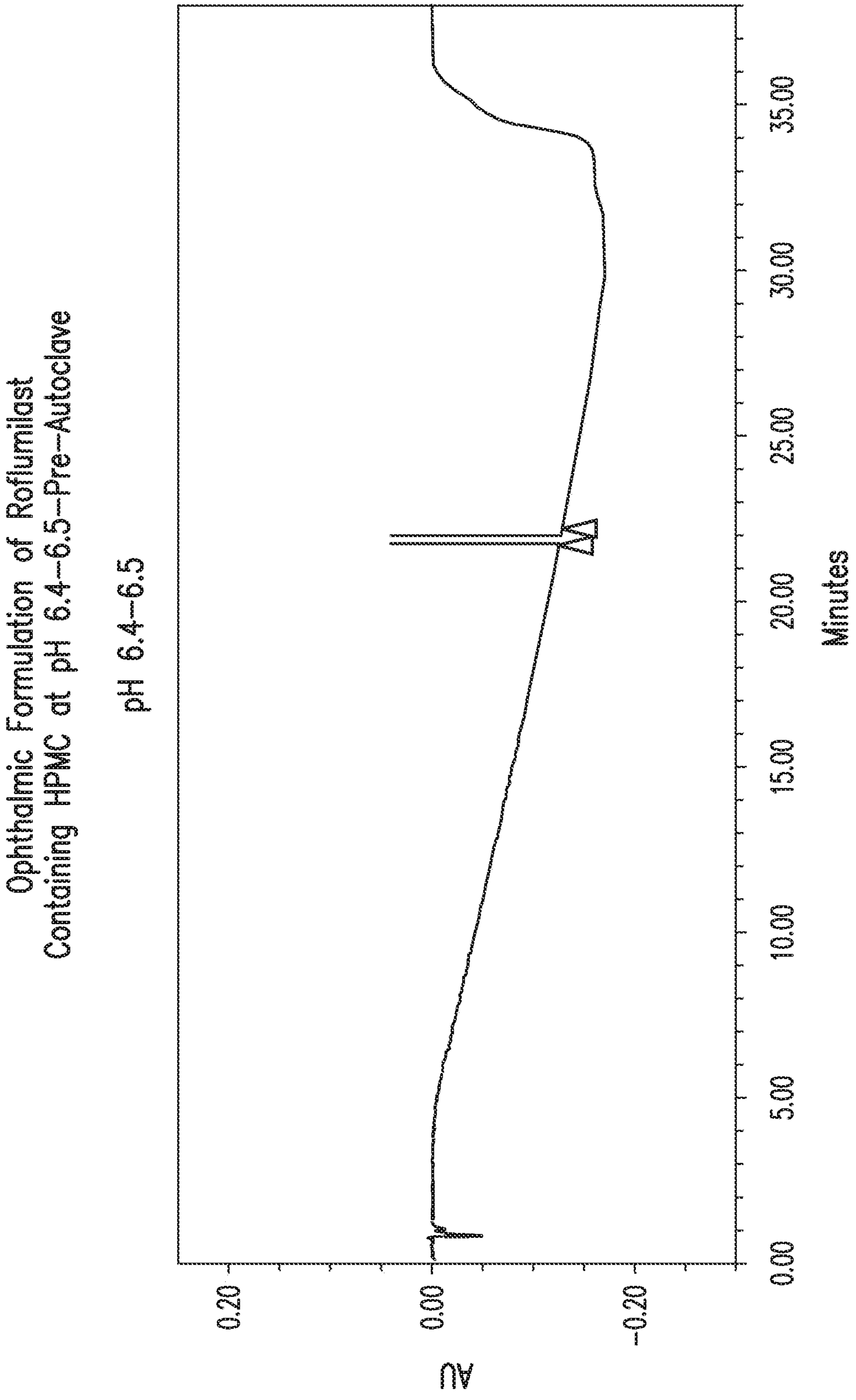
FIG. 5C is an HPLC chromatogram for an exemplary ophthalmic pharmaceutical composition comprising 0.10% roflumilast, 0.30% hydroxypropyl methylcellulose, 0.1% polysorbate, 0.45% phosphate, and 0.05% citrate at a pH of 6.4-6.5 under pre-autoclave conditions.
Figure 5D:
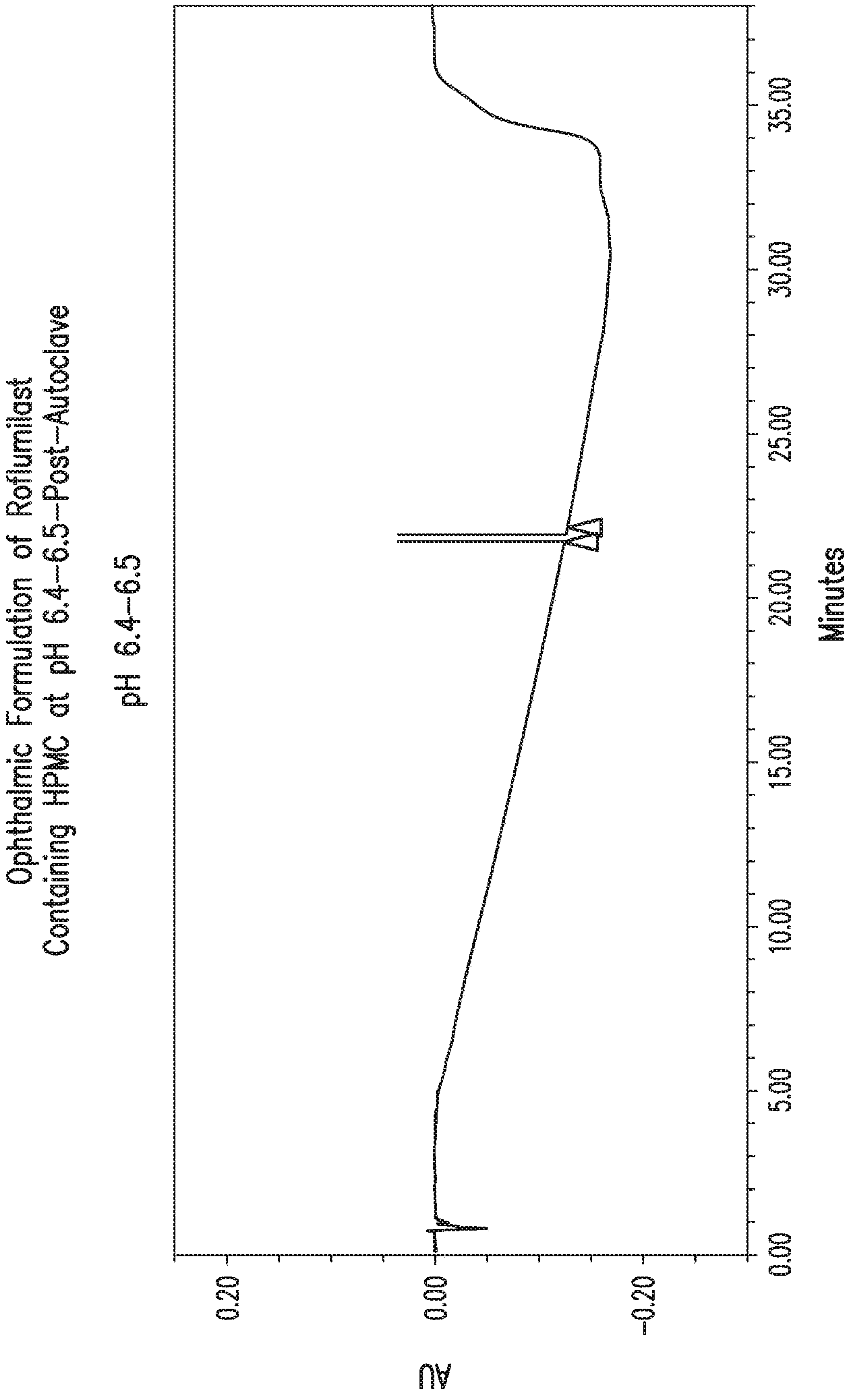
FIG. 5D is an HPLC chromatogram for an exemplary ophthalmic pharmaceutical composition comprising 0.10% roflumilast, 0.30% hydroxypropyl methylcellulose, 0.1% polysorbate, 0.45% phosphate, and 0.05% citrate at a pH of 6.4-6.5 under post-autoclave conditions.

Examples 1-4 were prepared having a pH of 7.4. The impurities of the formulations were measured using HPLC. HPLC assay was used to quantitate roflumilast and its impurities by checking the peak elution time relative to reference standards and measuring the peak areas. FIGS. 5A-D provides HPLC chromatograms for Example 1 pre-autoclave (FIGS. 5A and 5C) and post-autoclave (FIGS. 5B and 5D) sterilization cycle. FIGS. 5A and 5B provide HPLC chromatograms for Example 1 formulated at a final pH of 7.4, which illustrate detectable impurities due to hydrolysis of roflumilast under heat transfer. FIGS. 5C and 5D provide HPLC chromatograms for Example 1 formulated at a final pH of 6.4-6.5, which illustrate barely detectable impurities due lack of hydrolysis. FIGS. 6A-6D provides HPLC chromatograms for Example 4 pre-autoclave (FIGS. 6A and 6C) and post-autoclave (FIGS. 6B and 6D) sterilization cycle. FIGS. 6A and 6B provide HPLC chromatograms for Example 4 formulated at a final pH of 7.4, which illustrate detectable impurities due to hydrolysis of roflumilast under heat transfer. FIGS. 6C and 6D provide HPLC chromatograms for Example 4 formulated at a final pH of 6.4-6.5, which illustrate barely detectable impurities due lack of hydrolysis. The impurities of each of Examples 1-4 was determined to be approximately or greater than 0.25%. It was determined that the impurities were largely attributable to hydrolysis of roflumilast.

Examples 1 and 4 were re-formulated with a pH of 6.4-6.5. For the reformulated compositions having a pH of 6.4-6.5, a phosphate/citrate buffer was used in the amount of 0.25%/0.5% compared to 0.45%/0.5% used for the compositions having a pH of 7.4. The impurities of the Examples 1 and 4 were measured using the same methodology as described above (HPLC). The results of the analysis are set forth below in Table 7.

TABLE 7

HPLC Analysis of Examples 1 and 4 (pH of 6.4-6.5).

| | Example 1 (HPLC Potency) | Example 1 (HPLC - Related Substances) | Example 4 (HPLC Potency) | Example 4 (HPLC-Related Substances) |
|---|---|---|---|---|
| Pre-autoclave - stirred overnight | 93.30% | 0.00% | 98.30% | 0.00% |
| Post-autoclave - stirred overnight | 97.90 | 0.00% | 98.70% | 0.00% |

The impurities of Examples 1 and 4 (pH=6.4-6.5) were determined to be below the limit of quantification. It was determined that adjusting the pH of the ophthalmic pharmaceutical compositions to 6.4-6.5 reduced hydrolysis impurities to below the limit of quantification.

Example 11

The particle size distribution of the ophthalmic pharmaceutical compositions of Examples 1 to 4 having a pH of 7.4 was assessed. The size of particles suspended in liquid vehicle was evaluated using laser light scattering using the Horiba LA-950V2 Particle Size Analyzer. For each of Examples 1 to 4, the particle size distribution was assessed: (i) pre-autoclave; (ii) pre-autoclave after 3-minutes of sonicating; (iii) pre-autoclave after 3 minutes of sonicating and 7 days of storage; (iv) post-autoclave; (v) post-autoclave after 3-minutes of sonicating; and (vi) post-autoclave after 3 minutes of sonicating and 7 days of storage.

Comparative data for the suspension formulations of Examples 1 to 4 is provided below in Table 8. FIGS. 7 and 8 provides particle size distribution plots for Example 1 at a pH of 7.4 comparing non-autoclaved (FIG. 7) and autoclaved conditions (FIG. 8) with mixing and 7 days of storage. FIGS. 9 and 10 provides particle size distribution plots for Example 4 at a pH of 7.4 comparing non-autoclaved (FIG. 9) and autoclaved conditions (FIG. 10) with mixing and 7 days of storage.

TABLE 8

Particle Size Assessment of Examples 1-4 (pH 7.4; D90 Values)

| | Example 1 (D90 Values) | Example 2 (D90 Values) | Example 3 (D90 Values) | Example 4 (D90 Values) |
|---|---|---|---|---|
| Pre-autoclave | 6.9 μm | 8.5 μm | 5.86 μm | 10.9 μm |
| Pre-autoclave + 3-min sonicate | 6.6 μm | 8.1 μm | 5.5 μm | 8.3 μm |
| Pre-autoclave + sonicate + 7-day storage | 6.5 μm | 8 μm | 5.3 μm | 10.1 μm |
| Post-autoclave | 35.6 μm | 139.9 μm | 90.9 μm | 14.7 μm |
| Post-autoclave + 3-min sonicate | 35.3 μm | 42 μm | 15.9 μm | 12.5 μm |
| Post-autoclave + sonicate + 7-day storage | 21 μm | 34 μm | 17.5 μm | 16.9 μm |

Example 12

The particle size of ophthalmic pharmaceutical compositions of Examples 1 and 4 having a pH of 6.4-6.5 was assessed. For Examples 1 and 4, the particle size was assessed: (i) pre-autoclave after 60 minutes of stirring; (ii) pre-autoclave after overnight stirring; and (iii) post-autoclave after overnight stirring.

Comparative data for the suspension formulations of Examples 1 and 4 is provided below in Table 9. FIG. 11 provides particle size distribution plots for Example 1 at a pH of 6.4-6.5 comparing non-autoclaved and autoclaved conditions with stirring. FIG. 12 provides particle size distribution plots for Example 4 at a pH of 6.4-6.5 comparing non-autoclaved and autoclaved conditions with stirring. FIG. 13 includes a plot comparing the median particle size of Examples 1 and 4 at a pH of 6.4-6.5 comparing non-autoclaved and autoclaved conditions with stirring. FIG. 13 also includes the median particle size of the API, as well as HPLC potency results.

The data indicates that formulating at a pH of 6.4-6.5 mitigates particle size increase and polydispersity. The data suggests that a pH of 6.4-6.5 relative to pH of 7.4 reduced aggregation due to amide-hydrolysis.

TABLE 9

Particle Size Assessment of Examples 1 and 4 (pH 6.4-6.5; Median Particle Size and D90 Values)

| | Example 1 Median Particle Size | Example 1 (D90 Values) | Example 4 Median Particle Size | Example 4 (D90 Values) |
|---|---|---|---|---|
| Pre-autoclave + 60-minute stir | 9.68 μm | 179.1 μm | 8.04 μm | 99.3 μm |
| Pre-autoclave + Overnight stir | 5.36 μm | 9.5 μm | 5.51 μm | 10.4 μm |
| Post-autoclave + Overnight stir | 8.00 μm | 13.8 μm | 16.02 μm | 41.4 μm |

Example 13

The impact of dry heat sterilization on roflumilast was assessed. Bulk API of roflumilast was dried at 137° C. for 20 hours. The particle size of the roflumilast was measured. FIG. 14 provides a particle size distribution plot for the bulk API after dry heat sterilization. As illustrated in FIG. 14, dry heat sterilization does not significantly impact the particle size distribution of the API, which was reported as having a D90 of approximately 10 μm from the API manufacturer.

Example 14

The impact of terminal sterilization on the 0.1% pharmaceutical composition suspension of roflumilast set forth in Table 10 was assessed pre- and post-terminal sterilization.

TABLE 10

Ophthalmic Pharmaceutical Suspension of Roflumilast

| Ingredient | % w/v |
|---|---|
| Roflumilast | 0.1% w/v |
| Polyvinylpyrrolidone | 0.6% w/v |
| Tyloxapol | 0.3% w/v |
| Phosphate/Citrate Buffer | 0.25%/0.05% |
| Sodium Chloride | 0.7% |
| Water for injection | q.s. ad 1.0 mL |
| 1N HCl and/or 1N NaOH | As needed to adjust to pH of 6.5 |

Pharmaceutical compositions suspensions of roflumilast in 1 ml samples were terminally sterilized, and the particle size was assessed after a one week accelerated stability study (60° C.). As illustrated in FIGS. 15A-D, terminal gamma sterilization does not significantly impact the particle size distribution of the finished drug product. FIG. 15A illustrates the particle size distribution pre-terminal gamma sterilization. FIG. 15B illustrates the particle size distribution shortly post-terminal gamma sterilization (i.e., TO post-terminal gamma sterilization). FIG. 15C illustrates the particle size distribution three days post-terminal gamma sterilization. FIG. 15D illustrates the particle size distribution one week (seven days) post-terminal gamma sterilization.

The pH, osmolality, and impurities (RT, PA, and % PA) were also assessed for the three concentrations of the pharmaceutical composition set forth in Table 10. These properties were assessed pre-terminal gamma sterilization (pre-gamma TO) and at days 0, 3, and 7 post-terminal gamma sterilization (post-gamma day 0, day 3, and day 7) under accelerated stability conditions (60° C.). The results of the pH analysis are set forth in Table 11. As illustrated in Table 11, the pH only decreased minimally after terminal gamma sterilization.

TABLE 11

Impact of Gamma Sterilization on pH.

| | Pre-gamma (pH) | Post-gamma (pH) | | |
|---|---|---|---|---|
| | T0 | T0 | Day 3 | Day 7 |
| 0.1% Roflumilast | 6.52 | 6.18 | 6.02 | 6.04 |
| 0.3% Roflumilast | 6.5 | 6.16 | 6.03 | 5.86 |
| 1.0% | 6.5 | 6.23 | 6.10 | 6.03 |

The results of the osmolality analysis are set forth in Table 12. As illustrated in Table 12, there were no significant changes in osmolality following terminal gamma sterilization.

TABLE 12

Impact of Gamma Sterilization on Osmolality.

| | Pre-gamma (pH) | Post-gamma (pH) | | |
|---|---|---|---|---|
| | T0 | T0 | Day 3 | Day 7 |
| 0.1% Roflumilast | 250 | 257 | 261 | 264 |
| 0.3% Roflumilast | 253 | 245 | 257 | 274 |
| 1.0% Roflumilast | 249 | 252 | 263 | 272 |

As illustrated in Table 13, terminal gamma sterilization did not significantly impact the level of impurities. Only the 0.1% concentration formulation had impurities of less than 0.3%, while the other two concentrations did not have any impurities.

TABLE 13

| Impact of Gamma Sterilization on Impurities (RT, PA, % PA). | | | | | | | | | | | | |
|---|---|---|---|---|---|---|---|---|---|---|---|---|
| | Pre-gamma | | | Post-gamma | | | | | | | | |
| | T0 | | | Day 0 | | | Day 3 | | | Day 7 | | |
| | RT | PA | % PA | RT | PA | % PA | RT | PA | % PA | RT | PA | % PA |
| 0.1% | 0 | 0 | 0 | 2.089 | 8.5 | 0.251 | 2.118 | 6.2 | 0.198 | 2.082 | 9 | 0.297 |
| 0.3% | 0 | 0 | 0 | 0 | 0 | 0 | 0 | 0 | 0 | 0 | 0 | 0 |
| 1.0% | 0 | 0 | 0 | 0 | 0 | 0 | 0 | 0 | 0 | 0 | 0 | 0 |

Example 15

The impact of terminal sterilization on three different concentrations of suspensions of roflumilast was further assessed at three stability timepoints under three conditions to ensure that no appreciable degradation or increase in particle size had occurred over time, and to ensure that no further impurities would arise throughout storage at different temperatures (5, 25, and 40° C.). The pharmaceutical composition set forth in Table 10 (Example 14) was prepared with three different concentrations of roflumilast, 0.1%, 0.3%, and 1.0% roflumilast. As illustrated in FIGS. 15A 15B, and 15C, terminal gamma sterilization did not significantly impact the particle size in the sample at 1, 2, or 3 months for all three concentrations. Note that the data analysis for month 1 (the 0.1% concentration) was excluded due to a sample error, which was fixed in the second run (for the 0.3% concentration). Additionally, as illustrated in FIGS. 16A, 16B, and 16C, gamma sterilization did not significantly impact the level of impurities (all stayed below 0.5% of active drug, well below that percentage of all suspension materials).

The foregoing description has been presented for purposes of illustration and description. This description is not intended to limit the invention to the precise form disclosed. Persons of ordinary skill in the art will appreciate that modifications and substitutions of the basic inventive description may be made.

What is claimed is:

1. An ophthalmic pharmaceutical composition comprising:
- a therapeutically effective amount of roflumilast at about 0.3% w/v to about 1.0% w/v;
- a viscosity agent comprising hydroxypropyl methylcellulose at about 0.1% w/v to about 5.0% w/v;
- a surfactant at about 0.05% w/v to about 3.0% w/v; and
- a buffer at about 0.3% w/v to about 7.5% w/v,
- wherein the composition has a pH between 6.0 and 6.7, and
- wherein the composition has less than 0.25% of any roflumilast-related impurity as measured by high-performance liquid chromatography (HPLC).

2. The ophthalmic pharmaceutical composition of claim 1, wherein the surfactant is a polysorbate.

3. The ophthalmic pharmaceutical composition of claim 1, wherein the buffer is a phosphate and citrate buffer.

4. The ophthalmic pharmaceutical composition of claim 1, wherein the pharmaceutical composition is a suspension.

5. The ophthalmic pharmaceutical composition of claim 4, wherein the pharmaceutical composition has a particle size distribution characterized by a d90 value of from about 5 μm to about 25 μm.

6. The ophthalmic pharmaceutical composition of claim 4, wherein the pharmaceutical composition has a particle size distribution characterized by a d90 value of less than or equal to about 10 μm.

7. The ophthalmic pharmaceutical composition of claim 1, wherein the pharmaceutical composition retains a percentage of greater than 99% roflumilast following terminal sterilization.

8. An ophthalmic pharmaceutical composition comprising:
- a therapeutically effective amount of roflumilast at about 0.3% w/v to about 1.0% w/v;
- a viscosity agent comprising polyvinylpyrrolidone at about 0.1% w/v to about 5.0% w/v;
- a surfactant at about 0.05% w/v to about 3.0% w/v; and
- a buffer at about 0.3% w/v to about 7.5% w/v,
- wherein the composition has a pH between 6.0 and 6.7, and
- wherein the composition has less than 0.25% of any roflumilast-related impurity as measured by high-performance liquid chromatography (HPLC).

9. The ophthalmic pharmaceutical composition of claim 8, wherein the surfactant is a tyloxapol.

10. The ophthalmic pharmaceutical composition of claim 8, wherein the buffer is a phosphate and citrate buffer.

11. The ophthalmic pharmaceutical composition of claim 8, wherein the pharmaceutical composition is a suspension.

12. The ophthalmic pharmaceutical composition of claim 11, wherein the pharmaceutical composition has a particle size distribution characterized by a d90 value of from about 5 μm to about 25 μm.

13. The ophthalmic pharmaceutical composition of claim 11, wherein the pharmaceutical composition has a particle size distribution characterized by a d90 value of less than or equal to about 10 μm.

14. The ophthalmic pharmaceutical composition of claim 8, wherein the pharmaceutical composition retains a percentage of greater than 99% roflumilast following terminal sterilization.

15. An ophthalmic pharmaceutical composition comprising:
- a therapeutically effective amount of roflumilast at about 0.3% w/v to about 1.0% w/v;
- a viscosity agent comprising carboxymethyl cellulose at about 0.1% w/v to about 5% w/v;
- a surfactant at about 0.05% w/v to about 3.0% w/v; and
- a buffer at about 0.3% w/v to about 7.5% w/v,
- wherein the composition has a pH between 6.0 and 6.7, and
- wherein the composition has less than 0.25% of any roflumilast-related impurity as measured by high-performance liquid chromatography (HPLC).

16. The ophthalmic pharmaceutical composition of claim 15, wherein the surfactant is a polysorbate.

17. The ophthalmic pharmaceutical composition of claim 15, wherein the buffer is a phosphate and citrate buffer.

18. The ophthalmic pharmaceutical composition of claim 15, wherein the pharmaceutical composition is a suspension.

19. The ophthalmic pharmaceutical composition of claim 18, wherein the pharmaceutical composition has a particle size distribution characterized by a d90 value of from about 5 μm to about 25 μm.

20. The ophthalmic pharmaceutical composition of claim 18, wherein the pharmaceutical composition has a particle size distribution characterized by a d90 value of less than or equal to about 10 μm.

21. The ophthalmic pharmaceutical composition of claim 15, wherein the pharmaceutical composition retains a percentage of greater than 99% roflumilast following terminal sterilization.

22. A method of manufacturing a stable, ophthalmic pharmaceutical composition of roflumilast comprising:

(a) mixing about 0.3% to 1.0% w/v of roflumilast and at least one inactive ingredient to obtain a pharmaceutical composition having a pH of between 6.0 and 6.7;

(b) packaging the pharmaceutical composition; and (c) terminally sterilizing the pharmaceutical composition in the packaging by using gamma radiation.

* * * * *